US007022492B2

(12) United States Patent
Zheng et al.

(10) Patent No.: US 7,022,492 B2
(45) Date of Patent: Apr. 4, 2006

(54) ECSTASY HAPTENS AND IMMUNOGENS

(75) Inventors: Yi Feng Zheng, Wilmington, DE (US); Yali Yang, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 118 days.

(21) Appl. No.: 10/736,018

(22) Filed: Dec. 15, 2003

(65) Prior Publication Data

US 2005/0130225 A1   Jun. 16, 2005

(51) Int. Cl.
    *G01N 33/53*   (2006.01)
    *G01N 33/531*  (2006.01)
    *C07K 16/00*   (2006.01)
    *C07K 17/02*   (2006.01)
    *C07D 317/58*  (2006.01)

(52) U.S. Cl. .................... 435/7.9; 435/961; 435/975; 435/7.1; 435/188; 436/544; 436/546; 530/388.9; 530/389.8; 530/402; 530/403; 530/405; 424/175.1; 549/444; 549/443; 548/526

(58) Field of Classification Search ............... 549/444, 549/443; 435/961, 975, 7.1, 7.9, 188; 530/388.9, 530/389.8, 403, 405, 402; 436/546, 545, 436/544; 424/175.1; 548/526
See application file for complete search history.

(56) References Cited

U.S. PATENT DOCUMENTS

| | | | |
|---|---|---|---|
| 1,879,003 A | 9/1932 | Alles | 564/381 |
| 1,921,424 A | 8/1933 | Nabenhauer | 167/58 |
| 2,344,356 A | 3/1944 | Hildebrandt | 260/570.8 |
| 3,117,160 A | 1/1964 | Holland | 260/570.8 |
| 3,547,999 A | 12/1970 | Shulgin | 260/570.8 |
| 3,709,868 A | 1/1973 | Spector | 260/121 |
| 3,758,691 A | 9/1973 | Carlsson et al. | 424/330 |
| 3,763,218 A | 10/1973 | Kaiser et al. | 260/471 A |
| 3,766,162 A | 10/1973 | Spector | 260/112 R |
| 3,775,536 A | 11/1973 | Spector et al. | 424/1 |
| 3,847,950 A | 11/1974 | Suh et al. | 260/340.5 |
| 3,867,366 A | 2/1975 | Rubenstein et al. | 260/121 |
| 3,875,011 A | 4/1975 | Rubenstein et al. | 195/99 |
| 3,911,016 A | 10/1975 | Klingler et al. | 260/570.8 R |
| 3,995,021 A | 11/1976 | Gross | 424/1.5 |
| 3,996,344 A | 12/1976 | Gross | 424/1.5 |
| 4,016,146 A | 4/1977 | Soares | 260/112 R |
| 4,022,878 A | 5/1977 | Gross | 424/1.5 |
| 4,036,823 A | 7/1977 | Soares | 260/112 R |
| 4,041,076 A | 8/1977 | Avenia et al. | 260/559 A |
| 4,058,642 A | 11/1977 | Renth et al. | 424/330 |
| 4,064,228 A | 12/1977 | Gross | 424/1 |
| 4,073,798 A | 2/1978 | Suh | 260/340.5 R |
| 4,097,586 A | 6/1978 | Gross | 424/1 |
| 4,129,598 A | 12/1978 | Giudicelli et al. | 260/570.8 R |
| 4,218,539 A | 8/1980 | Weltman | 435/188 |
| 4,220,565 A | 9/1980 | Katz | 260/6 |
| 4,329,281 A | 5/1982 | Christenson et al. | 260/112 B |
| 4,595,656 A | 6/1986 | Allen et al. | 435/7 |
| 4,680,338 A | 7/1987 | Sundoro | 525/54.1 |
| 4,686,181 A | 8/1987 | Dona | 435/7 |
| 4,760,142 A | 7/1988 | Primes et al. | 544/287 |
| 4,843,147 A | 6/1989 | Levy et al. | 530/391 |
| 4,847,195 A | 7/1989 | Khanna et al. | 435/7 |
| 4,868,132 A | 9/1989 | Byrnes et al. | 436/546 |
| 4,952,336 A | 8/1990 | Brynes et al. | 252/301.16 |
| 4,990,443 A | 2/1991 | Huber et al. | 435/7.9 |
| 5,026,827 A | 6/1991 | Miyazaki et al. | 530/405 |
| 5,101,015 A | 3/1992 | Brynes et al. | 530/363 |
| 5,135,863 A | 8/1992 | Hu et al. | 435/188 |
| 5,145,791 A | 9/1992 | Zeitvogel et al. | 436/546 |
| 5,198,587 A | 3/1993 | Imai et al. | 564/374 |
| 5,227,472 A | 7/1993 | Yoshioka | 530/403 |
| 5,233,025 A | 8/1993 | Miyazaki et al. | 530/388.9 |
| 5,256,409 A | 10/1993 | Blincko | 424/85.8 |
| 5,262,333 A | 11/1993 | Heiman et al. | 436/537 |
| 5,266,720 A | 11/1993 | Gallacher et al. | 560/60 |
| 5,270,166 A | 12/1993 | Parsons et al. | 435/7.4 |
| 5,294,638 A | 3/1994 | Hell et al. | 514/452 |
| 5,328,828 A | 7/1994 | Hu et al. | 435/7.9 |
| 5,336,621 A | 8/1994 | Primes et al. | 436/534 |
| 5,354,693 A | 10/1994 | Brynes et al. | 436/537 |
| 5,372,949 A | 12/1994 | Zeitvogel et al. | 436/546 |
| 5,373,092 A | 12/1994 | Gallacher et al. | 435/7.93 |
| 5,424,204 A | 6/1995 | Aoyama et al. | 435/188 |
| 5,470,997 A | 11/1995 | Buechler et al. | 558/254 |
| 5,492,841 A | 2/1996 | Craig | 436/534 |
| 5,501,987 A | 3/1996 | Ordonez et al. | 436/534 |
| 5,514,559 A | 5/1996 | Markert-Hahn et al. | 435/7.92 |
| 5,518,887 A | 5/1996 | Parsons et al. | 435/7.1 |
| 5,525,524 A | 6/1996 | Buechler et al. | 436/518 |
| 5,610,283 A | 3/1997 | Buechler | 530/404 |
| 5,616,503 A | 4/1997 | Self | 436/518 |

(Continued)

FOREIGN PATENT DOCUMENTS

DE        2844427        4/1980

(Continued)

*Primary Examiner*—Mary E. Ceperley
*Assistant Examiner*—Shafigul Haq
(74) *Attorney, Agent, or Firm*—Theodore J. Leitereg

(57) ABSTRACT

Methods, compositions and kits are disclosed. Enzyme conjugates of Formula I are employed in assays for the determination of an methylenedioxyamphetamine, a methylene-dioxyethamphetamine, and/or a methylene-dioxymethamphetamine. Immunogenic conjugates of Formula I are employed to prepare antibodies for an methylenedioxyamphetamine, a methylenedioxyethamphetamine, and/or for a methylene-dioxymethamphetamine for use in assays for the determination of an methylenedioxyamphetamine, a methylenedioxyethamphetamine, and/or a methylene-dioxymethamphetamine. The enzyme conjugates may also be employed to screen antibodies for use in such methods.

68 Claims, 9 Drawing Sheets

U.S. PATENT DOCUMENTS

| | | | |
|---|---|---|---|
| 5,643,732 A | 7/1997 | Strahilevitz | 435/7.1 |
| 5,840,588 A | 11/1998 | Strahilevitz | 436/518 |
| 5,851,776 A | 12/1998 | Valkirs | 435/7.1 |
| 5,976,812 A | 11/1999 | Huber et al. | 435/7.1 |
| 6,033,890 A | 3/2000 | Jakobovits et al. | 435/190 |
| 6,090,567 A | 7/2000 | Jakobovits et al. | 435/7.9 |
| 6,140,137 A | 10/2000 | Sigler et al. | 436/536 |
| 6,214,859 B1 | 4/2001 | Yoneda et al. | 514/419 |
| 2003/0170917 A1 | 9/2003 | Hui et al. | 436/547 |
| 2003/0175995 A1 | 9/2003 | Hui | 436/547 |

FOREIGN PATENT DOCUMENTS

| | | | |
|---|---|---|---|
| EP | 828880 | 7/1958 | |
| EP | 1467560 | 11/1975 | 317/58 |
| EP | 0 183901 A2 | 11/1985 | 33/531 |
| EP | 0 517325 A2 | 6/1992 | 33/532 |
| EP | 1 321772 A1 | 12/2002 | 33/94 |
| EP | 1340981 A2 * | 9/2003 | |
| GB | 2361473 A * | 10/2001 | |
| JP | 53066417 A | 6/1978 | 436/534 |
| JP | 56125666 A | 10/1981 | 436/537 |
| JP | 63220932 | 9/1988 | 530/388.9 |
| JP | 2069196 A | 3/1990 | |
| WO | WO 86/05189 | 9/1986 | 33/531 |
| WO | WO 90/15798 | 12/1990 | |

* cited by examiner

ECSTASY HAPTENS AND IMMUNOGENS

BACKGROUND OF THE INVENTION

Field of the Invention

This invention relates to methods, compositions and kits for detecting the presence and/or amounts of entactogens in samples suspected of containing the same. In particular, the invention relates to haptens, immunogens and assays for 3,4-methylenedioxyamphetamine (MDA), 3,4-methylenedioxy-methamphetamine (MDMA) and 3,4-methylenedioxy-ethylamphetamine (MDEA).

The clinical diagnostic field has seen a broad expansion in recent years, both as to the variety of materials of interest that may be readily and accurately determined, as well as the methods for the determination. Over the last decade, testing for drugs of abuse has become commonplace. This testing is not only for the monitoring of criminal offenders and drug addicts, but employers also use it for the screening of workers. In recent years, immunoassay based on the reaction of an antibody with an antigen has been extensively investigated for this purpose. Immunoassay may be roughly classified into radioimmunoassay, using a radioactive isotope, enzyme-immunoassay (EIA) using an enzyme and luminescence assays, using fluorescent labels, e.g., fluorescence polarization, and chemiluminescent labels.

Amphetamine and methamphetamine stimulate the central nervous system and have been used medicinally to treat hypotension, narcolepsy and obesity. Because of their stimulating effects, the drugs and derivatives have been abused.

The designer drugs, methylenedioxyamphetamine (MDA), 1-3',4'-methylene-dioxyphenyl)-2-propanamine, "Love Pills", methylenedioxymethamphetamine (MDMA), "Adam", "Ecstasy" and methylenedioxyethylamphetamine (MDEA), "Eve" are entactogens, producing feeling of euphoria and friendliness. These drugs are currently popular and called "rave drugs". It has been demonstrated by several experimental studies on rats and human that these drugs are risky to human. In fact, toxicity and deaths associated with MDMA has been reported. Recent reviews have also reported the hepatotoxicity, neurotoxicity, psychopathology and the abuse potential of these drugs. The common use of these drugs has been widespread in the world and appeared recently as the most popular drug of abuse in certain countries.

Although there is a need for the detection of MDMA, MDA and its metabolites such as 4-hydroxy-3-methoxymethamphetamine (HMMA) and so forth, the literature discloses GC-MS, HPLC detection methods, which are expensive and time consuming. It appears that researchers have tried to use existing amphetamine/methamphetamine immunoassay technology for the detection of MDMA and MDA due to their cross-reactivity. The hope was that the antibody recognizing amphetamine and methamphetamine would also be useful for assays for MDMA, MDA or its metabolites. For instance, three commercial amphetamine/methamphetamine assays, namely, EMIT®, FPIA and RIA, have been investigated for the detection of MDA, MDMA and MDEA. (Ruangyuttikam, et al., "Comparison of three commercial amphetamine immunoassay for detection of methamphetamine, methylenedioxyamphetamine, methylenedioxy-methamphetamine and methylenedioxyethylamphetamine" J. Anal. Toxicol. 1988, 12, 229; Kunsman, et al., "Application of the Syva Emit and Abbott TDX amphetamine Immunoassays to the detection of 3,4-Methylene-dioxy-methamphetamine (MDMA) and 3,4-Methylene-dioxyethamphetamine (MDEA) in Urine" J. Anal. Toxicol. 1990, 14, 149; Cody, J. T. "Detection of D, L-amphetamine, D,L-methamphetamine, and illicit amphetamine analogs using diagnostic products corporation's amphetamine and methamphetamine radioimmunoassay" J. Anal. Toxicol. 1990, 14, 321; Ensslin, et al., "Toxicological detection of the designer drug 3,4-methylenedioxyethamphetamine (MDE, 'Eve') and its metabolites in urine by gas chromatography spectrometry and fluorescence polarization immunoassay" J. Chromatogr. 1996, B683, 189.

However, according to the published literature, the above approaches have achieved little, if any, success. This result is not unexpected due to the very different chemical structures between methamphetamine and MDMA analogs. That is, MDMA and MDA have an extra (methylenedioxy) five-member ring in comparison to methamphetamine and amphetamine, respectively.

There is, therefore, a need for assays for the detection of the aforementioned designer drugs and, in some instances, their major metabolites. The assays should be able to detect the designer drugs in order to monitor and treat patients addicted to these drugs.

SUMMARY OF THE INVENTION

One embodiment of the present invention is a compound of the formula:

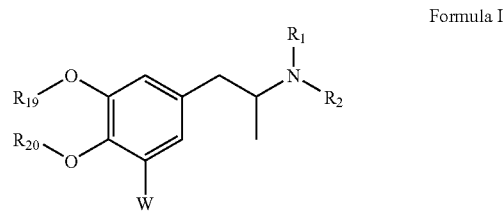

Formula I wherein:
  $R^{19}$ is lower alkyl or is taken together with $R^{20}$ to form a ring, which may be a five- or six-member ring;
  $R^{20}$ is lower alkyl, or is taken together with $R^{19}$ to form a ring as discussed above,
  $R^1$ is H or lower alkyl,
  $R^2$ is H, lower alkyl, a protecting group or
    (a) —$(CH_2)_aC(O)(CH_2)_bSR^3$, wherein a is 0 to 5, b is 1 to 5 and $R^3$ is H or lower alkyl or $(CH^2)_cC(O)NR^4R^5$ wherein c is 1 to 5, $R^4$ is H or lower alkyl and $R^5$ is H, an immunogenic carrier or a label, or
    (b) $(A)_d(Q)_n$ wherein Q is H or —$(CH_2)_eCH(R^8)(CH_2)_fOC(O)(CH_2)_gR^9$ being H only when d is 1 wherein A is —$C(O)(CH_2)_hC(O)NR^{10}((CH_2)_jO(CH_2)_kO)_m(CH)_2NR^{11}$—, d is 0 or 1, n is 0 or 1 wherein one of d or n is 1, h is 1 to 5, $R^{10}$ is H or lower alkyl, j is 1 to 5, k is 1 to 5, m is 1 to 3, $R^{11}$ is H or lower alkyl, e is 1 to 5, $R^8$ is OH or H, f is 1 to 5, g is 0 to 5, and $R^9$ is H, an immunogenic carrier or a label;
  W is H or $JR^{14}$ being H when $R^2$ is other than H or lower alkyl, wherein
  J is O or S,
  $R^{14}$ is H, lower alkyl, a protecting group, or
    —$(CH_2)_rC(O)NR^{15}(CH_2)_s(D)_tR^{16}$, wherein r is 1 to 5, $R^{15}$ is H or lower alkyl, s is 1 to 5, D is S, O, or N H, t is 0 or 1 being 0 when $R^{16}$ is maleimidyl or succinimidyl, $R^{16}$ is H, maleimidyl, succinimidyl, or —$(CH_2)_qC(O)NR^{17}R^{18}$, q is 1 to 5,
R$^{17}$ is H or lower alkyl,
R$^{18}$ is H, lower alkyl, an immunogenic carrier or label, and including the acid salts thereof.

Another embodiment of the present invention is a compound of the formula:

Formula II

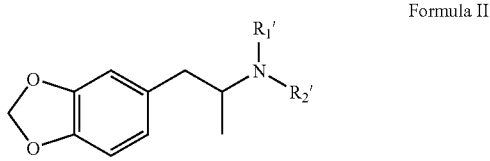

wherein:
R$^{1\prime}$ is H, lower alkyl or a protecting group,
R$^{2\prime}$ is a protecting group, or
  (a) —(CH$_2$)$_a$C(O)(CH$_2$)$_b$SR$^{3\prime}$, wherein a is 0 to 5, b is 1 to 5 and R$^{3\prime}$ is H or lower alkyl or (CH$_2$)$_c$C(O)NR$^{4\prime}$R$^{5\prime}$ wherein c is 1 to 5, R$^{4\prime}$ is H or lower alkyl and R$^{5\prime}$ is H, an immunogenic carrier or a label, or
  (b) (A)$_d$(Q)$_n$ wherein Q is H or —(CH$_2$)$_e$CH(R$^{8\prime}$)(CH$_2$)$_f$OC(O)(CH$_2$)$_g$R$^{9\prime}$ being H only when d is 1 wherein A is —C(O)(CH$_2$)$_h$C(O)N(R$^{10}$)((CH$_2$)$_j$O(CH$_2$)$_k$O)$_m$(CH)$_p$NR$^{11}$—, d is 0 or 1, n is 0 or 1 wherein one of d or n is 1, h is 1 to 5, R$^{10}$ is H or lower alkyl, j is 1 to 5, k is 1 to 5, m is 1 to 3, R$^{11}$ is H or lower alkyl, e is 1 to 5, R$^{8\prime}$ is OH or H, f is 1 to 5, g is 0 to 5, and R$^{9\prime}$ is H, an immunogenic carrier or a label, and including the acid salts thereof.

Another embodiment of the present invention is a compound of the formula:

Formula III

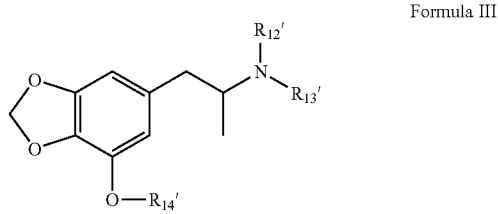

wherein:
R$^{12\prime}$ is H or lower alkyl,
R$^{13\prime}$ is H or lower alkyl,
R$^{14\prime}$ is a protecting group, or —(CH$_2$)$_r$C(O)NR$^{15\prime}$(CH$_2$)$_s$(D)$_t$R$^{16\prime}$, wherein r is 1 to 5, R$^{15}$, is H or lower alkyl, s is 1 to 5, D is S, O, or NH, t is 0 or 1 being 0 when R$^{16\prime}$ is maleimidyl or succinimidyl, R$^{16\prime}$ is H, a protecting group, maleimidyl or succinimidyl, or —(CH$_2$)$_q$C(O)NR$^{17\prime}$R$^{18\prime}$, wherein q is 1 to 5,
R$^{17\prime}$ is H, lower alkyl or a protecting group,
R$^{18\prime}$ is H, lower alkyl, a protecting group, an immunogenic carrier or a label, and including the acid salts thereof.

Another embodiment of the present invention is a method for determining a compound selected from the group consisting of 3,4-methylenedioxyamphetamine (MDA), 3,4-methylenedioxy-methamphetamine (MDMA) and 3,4-methylenedioxy-ethylamphetamine (MDEA). The method comprises providing in combination in a medium (i) a sample suspected of containing the compound and (ii) an antibody raised against a compound of Formula I, Formula II or Formula III that comprises a protein. The medium is examined for the presence of a complex comprising the compound and the antibody where the presence of such as complex indicates the presence of the compound in the sample. In one aspect of the above embodiment, the combination further comprises a label conjugate of the above compound.

Another embodiment of the present invention is a kit for determining a compound selected from the group consisting of 3,4-methylenedioxyamphetamine (MDA), 3,4-methylenedioxy-methamphetamine (MDMA) and 3,4-methylenedioxy-ethylamphetamine (MDEA). The kit comprises (a) an antibody raised against a compound of Formula I, Formula II or Formula III that comprises a protein and (b) ancillary reagents for determining the compound. The kit may further comprise (c) a label conjugate of the compound of the above formula.

DESCRIPTION OF THE SPECIFIC EMBODIMENTS

Figure 1:
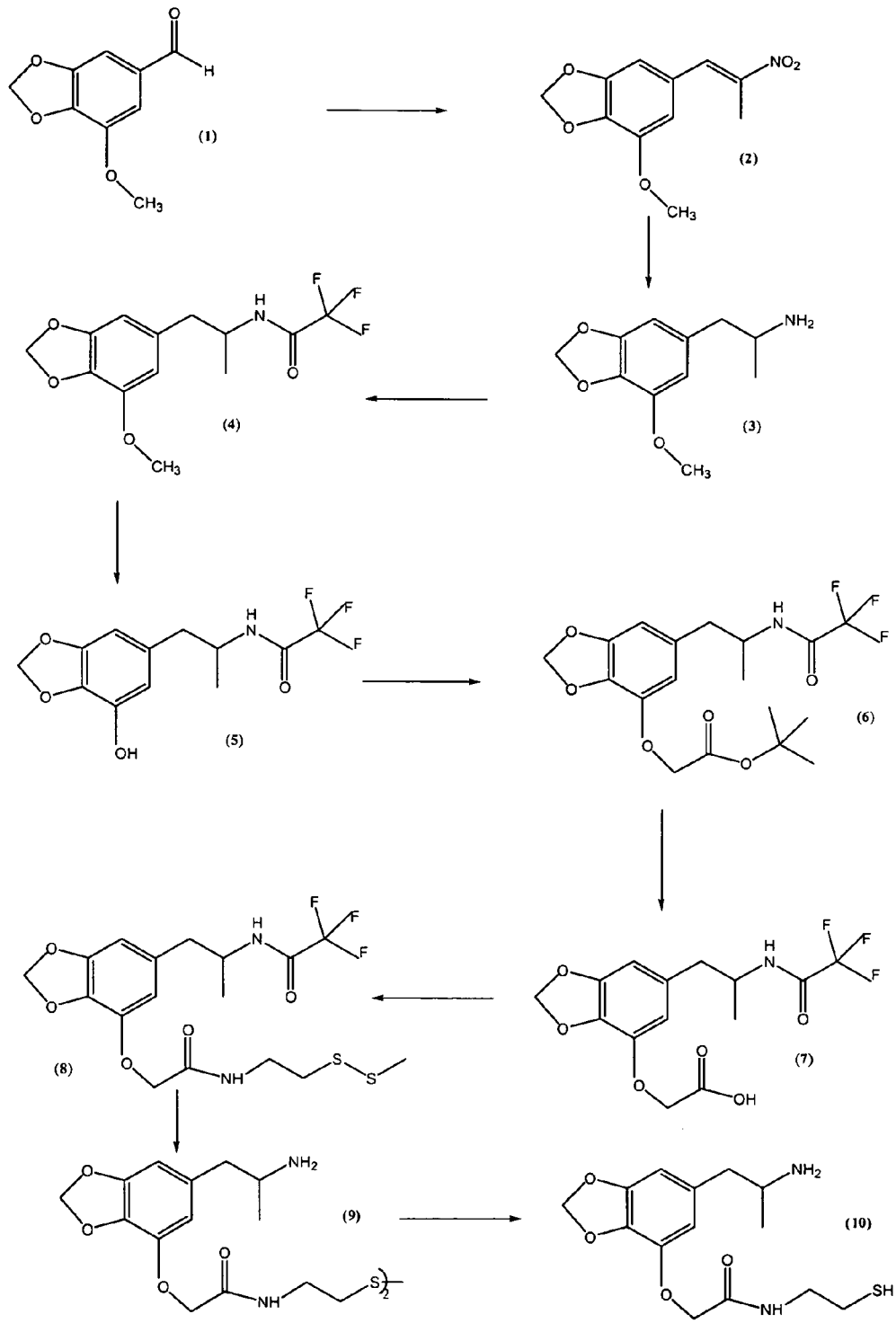
FIG. 1 is a reaction scheme depicting an example of a synthesis of an MDA hapten (10).

The present invention permits effective screening of samples for the presence of one or more entactogens as referred to above. Immunogens comprising proteins are synthesized and used to prepare antibodies specific for 3,4-methylenedioxyamphetamine (MDA), 3,4-methylenedioxy-methamphetamine (MDMA) and 3,4-methylenedioxy-ethylamphetamine (MDEA). The antibodies may be used in methods for detecting the aforementioned drugs in samples suspected of containing the drugs. Label conjugates are prepared and may be employed in the above methods.

The immunogens and label conjugates may involve an analog of MDA, MDMA or MDEA linked through the primary nitrogen atom or through an ether linkage on the benzene ring, to a protein or a label, respectively. The linking group may comprise about 2 to about 50 atoms, 4 to about 30 atoms, not counting hydrogen and may comprise a chain of from 2 to about 30 atoms, 3 to about 20 atoms, each independently selected from the group normally consisting of carbon, oxygen, sulfur, nitrogen, and phosphorous.

The number of heteroatoms in the linking groups will normally range from about 0 to about 20, 1 to about 15, 2 to about 10. The linking groups may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a carboxylic acid or phosphate acid and an alcohol are linked, esters are formed. Various linking groups are well known in the art; see, for example, Cautrecasas, *J. Biol. Chem.* (1970) 245: 3059.

The terms "amphetamine moiety" and "methamphetamine moiety" also include derivatives of amphetamine and methamphetamine such as, for example, esters, amides, haloacetamides, and the like.

One set of derivatives involves moieties wherein the amphetamine or methamphetamine is protected with a protecting group. Suitable types of protecting groups are well known in the art and have been described in detail in numerous patents and articles in the technical literature. See, for example, "Principles of Peptide Synthesis" (M. Bodanszky, Springer Verlag, Berlin, Heidelberg, New York, Tokyo (1984). Such protecting groups include, by way of example and not limitation, t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobomyl-oxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, formyl, and the like. Also included in the above compounds are salts thereof, particularly, salts involving the amine group of the amphetamine and/or methamphetamine. In one embodiment the salts are acid salts, i.e., salts formed with acids such as mineral acids, for example, hydrochloric acid, hydroboric acid, and the like, organic acids, for example, trifluoroacetic acid, acetic acid, DL-tartaric acid, and so forth.

As mentioned above, compounds include compounds of the formula:

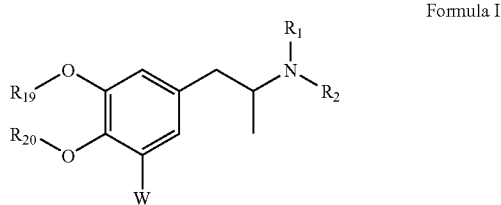

Formula I wherein:
$R^{19}$ is lower alkyl or is taken together with $R^{20}$ to form a ring, which may be a five- or six-member ring, usually a five-member ring;
$R^{20}$ is lower alkyl, or is taken together with $R^{19}$ to form a ring as discussed above,
$R^1$, is H or lower alkyl,
$R^2$ is H, lower alkyl, a protecting group or
   (a) $-(CH_2)_aC(O)(CH_2)_bSR^3$, wherein a is 0 to 5, 1 to 4, 1 to 3, 2 to 4, 1 to 2, b is 1 to 5, 1 to 4, 1 to 3, 2 to 4, 1 to 2, and $R^3$ is H or lower alkyl or $(CH^2)_cC(O)NR^4R^5$ c is 1 to 5, wherein $R^4$ is H or lower alkyl and $R^5$ is H, an immunogenic carrier or a label, or
   (b) $(A)_d(Q)_n$ wherein Q is H or $-(CH_2)_eCH(R^8)(CH_2)_fOC(O)(CH_2)_gR^9$ being H only when d is 1 wherein A is $-C(O)(CH_2)_hC(O)NR^{10}((CH_2)_jO(CH_2)_kO)_m(CH)_2NR^{11}-$, d is 0 or 1, n is 0 or 1 wherein one of d or n is 1, h is 1 to 5, 1 to 4, 1 to 3, 2 to 4, 1 to 2, $R^{10}$ is H or lower alkyl, j is 1 to 5, 1 to 4, 1 to 3, 2 to 4, 1 to 2, k is 1 to 5, 1 to 4, 1 to 3, 2 to 4, 1 to 2, m is 1 to 3, 1 to 2, $R^{11}$ is H or lower alkyl, e is 1 to 5, 1 to 4, 1 to 3, 2 to 4, 1 to 2, $R^8$ is OH or H, f is 1 to 5, 1 to 4, 1 to 3, 2 to 4, 1 to 2, g is 0 to 5, 1 to 4, 1 to 3, 2 to 4, 1 to 2, and $R^9$ is H, an immunogenic carrier or a label;
W is H or $JR^{14}$ being H when $R^2$ is other than H or lower alkyl, wherein
   J is O or S,
   $R^{14}$ is H, lower alkyl, a protecting group, or $-(CH_2)_rC(O)NR^{15}(CH_2)_s(D)_tR^6$, wherein r is 1 to 5, 1 to 4, 1 to 3, 2 to 4, 1 to 2, $R^{15}$ is H or lower alkyl, s is 1 to 5, 1 to 4, 1 to 3, 2 to 4, 1 to 2, D is S, O or NH, t is 0 or 1 being 0 when $R^{16}$ is maleimidyl or succinimidyl, $R^{16}$ is H, maleimidyl, succinimidyl, or $-(CH_2)_qC(O)NR^{17}R^{18}$, wherein q is 1 to 5, 1 to 4, 1 to 3, 2 to 4, 1 to 2,
   $R^{17}$ is H or lower alkyl,
   $R^{18}$ is H, lower alkyl, an immunogenic carrier or label, and including the acid salts thereof.

In some embodiments $R^2$ is $-(CH_2)_cC(O)DR^6$, wherein c is 2 to 6, 3 to 5, 2 to 4, D is O, S or NR7 wherein $R^7$ is H or lower alkyl, and $R^6$ is H, an immunogenic carrier or a label.

Specific embodiments of the above compounds of Formula I include:

A compound according to Formula I wherein $R^1$ is H and $R^2$ is H.

A compound according to Formula I wherein $R^1$ is H and $R^2$ is lower alkyl.

A compound according to Formula I wherein $R^{16}$ is $-(CH^2)_qC(O)NR^{17}R^{18}$ and $R^{18}$ is a poly(amino acid).

A compound according to Formula I wherein $R^1$ is H or lower alkyl, W is H and $R^2$ is —$(CH_2)_aC(O)(CH_2)_bSR^3$, wherein $R^3$ is —$(CH_2)_cC(O)NR^4R^5$ wherein $R^4$ is H or lower alkyl and $R^5$ is a poly(amino acid).

A compound according to Formula I wherein $R^1$ is H or lower alkyl, W is H and $R^2$ is $(A)_d(Q)_n$ wherein d is 0, n is 1, Q is —$(CH_2)_eCH(R^8)(CH_2)_fOC(O)(CH_2)_gR^9$ and $R^9$ is a poly(amino) acid.

A compound according to Formula I wherein $R^1$ is H or lower alkyl, W is H and $R^2$ is $(A)_d(Q)_n$ wherein d is 1, n is 1, Q is —$(CH_2)_eCH(R^8)(CH_2)_fOC(O)(CH_2)_gR^9$ and A is —$C(O)(CH_2)_hC(O)NR^{10}((CH_2)_jO(CH_2)_k O)_m(CH_2)_2 NR^{11}$—, and $R^9$ is a poly(amino) acid.

By the term "lower alkyl" is meant a branched or unbranched saturated monovalent hydrocarbon radical containing 1 to 10, usually, 1 to 5, carbon atoms, such as methyl, ethyl, propyl, butyl and pentyl, and including the normal, secondary, tertiary, and the like, forms thereof where appropriate.

By the term "acid salts" is meant salts formed with acids such as mineral acids, for example, hydrochloric acid, and the like, organic acids, for example, trifluoroacetic acid and the like.

By "-succinimidyl" is meant the following:

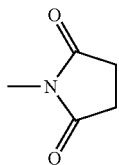

By "-maleimidyl" is meant the following:

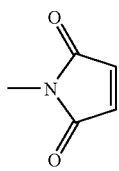

By the term "label" is meant a member of a signal producing system. The label is capable of being detected directly or is detectable through a specific binding reaction that produces a detectable signal. The labels generally are radioisotopic, luminescent, particulate or enzymic. The label can be a poly(amino acid), or protein, or a non-poly(amino acid), isotopic or non-isotopic, usually non-isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The term "non-poly(amino acid) labels" are those labels that are not proteins such as enzymes. A non-poly(amino acid) label may be a member of a signal producing system. The non-poly(amino acid) label is capable of being detected directly or is detectable through a specific binding reaction that produces a detectable signal. The non-poly(amino acid) labels generally are radioisotopic, luminescent, particulate, polynucleotidic or the like. More particularly, the label can be isotopic or non-isotopic, usually non-isotopic, and can be a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The signal producing system may have one or more components, at least one component being the label. The signal producing system generates a signal that relates to the presence of an entactogen in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508,178 (Rose, et al.), the relevant disclosure of which is incorporated herein by reference.

By the term "immunogenic carrier" is meant a group which, when conjugated to a hapten and injected into a mammal, will induce an immune response and elicit the production of antibodies that bind to the hapten. Haptens are compounds capable of binding specifically to corresponding antibodies, but do not themselves act as immunogens (or antigens) for preparation of the antibodies. Antibodies that recognize a hapten can be prepared against compounds comprised of the hapten linked to an immunogenic (or antigenic) carrier. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Immunogenic carriers include proteins such as, for example, albumins, serum proteins, e.g., globulins, ocular lens proteins and lipoproteins, and so forth. Illustrative proteins include bovine serum albumin (BSA), keyhole limpet hemocyanin ("KLH"), egg ovalbumin, bovine gamma-globulin (BGG) and the like.

A protein may be attached to a linking group by means of an amine group on the protein. The above formulas show the nitrogen atom of the amine group of the protein.

Enzyme conjugates may be prepared from compounds in accordance with the present invention. In general, functional groups suitable for attaching the compound to the enzyme are usually an activated ester or alkylating agent when the amino acid(s) that are to be conjugated on the enzyme have amino or hydroxyl groups and are usually alkylating agents or the like when the amino acid(s) that are to be conjugated on the enzyme comprise a sulfur atom such as, e.g., a cysteine. A large number of suitable functional groups are available for attaching to amino groups and alcohols such as activated esters including imidic esters, sulfonic esters and phosphate esters, activated nitrites, aldehydes, ketones, alkylating agents and the like. Conjugation of haptens to proteins using these and other attaching groups are well known in the art and are described in reviews such as for example, Maggio, E. T. "Enzyme-Immunoassay" (CRC Press, Boca Raton, Fla., 1980), Chapter 4, which contains an assortment of conjugation techniques; pages 81–88 of which are incorporated herein by reference.

Following reaction of the enzyme with a compound such as discussed above to form a conjugate, the product is then optionally purified as may be required. The purification and characterization of poly(amino acid)-hapten conjugates has been described in detail Maggio, et al.; "enzyme-immunoassay" (CRC Press, Boca Raton, Fla., 1980), Chapter 4, pages 86–88 of which are incorporated herein by reference. For example, if the conjugate is a mutant G6PDH-hapten conjugate, the purification can be by dialysis against aqueous/organic and aqueous solutions such as water/DMF or water, or by gel filtration chromatography on supports such as Sephadex, and the like.

As mentioned above, the conjugation can involve binding of a hapten to a free thiol group present on an amino acid side chain of the enzyme (e.g. cysteine). Such conjugation involves alkylation of the thiol sulfur atom by treatment with an electrophilic compound such as an alpha- or beta-unsaturated amide, ketone, ester, or the like, or an alkylating agent such as a reactive halide, e.g., bromide, or sulfonate or the like or reaction with an active disulfide such as a 2-nitro-4-carboxyphenyl disulfide. Specific examples by way of illustration and not limitation include alpha-bromoamides, maleimides, vinyl sulfones, alpha-iodoketones, and the like.

Conjugation reactions with enzymes can be affected by a number of factors. These include, but are not confined to, pH, temperature, buffer, ionic strength, substances which may protect the enzyme active site, amount and type of cosolvent, reaction time, and activation chemistry. A range of pH values from about 5.0 to about 9.5 can usually be used for conjugation reactions. These reactions are generally carried out at about 0 to about 40 degrees C., preferably about 4 to about 20 degrees C.

A number of buffers and salts, both alone and in combination, can be used for such reactions. These include Tris, bicarbonate, phosphate, pyrophosphate, EDTA, KCl, NaCl, and many others. The active site may be protected by substrates (i.e. glucose-6-phosphate and compounds that react reversibly with lysine (i.e. pyridoxal) to reduce deactivation of the enzyme during conjugation.

Cosolvents which may enhance hapten solubility include, but are not limited to, dimethylformamide, carbitol, dimethyl sulfoxide, 1-Methyl-2-pyrrolidinone, and 1,3-Dimethyl-3,4,5,6-tetrahydro 2(1H)-pyrimidinone. These may be useful as about 1 to about 30% of the reaction volume. Reactions can vary from about 15 minutes to many days, depending on the activation chemistry. Carboxylic compounds may be activated to form esters with N-Hydroxysuccinimide or its sulfo-analog, or to mixed anhydrides through reaction with carbitol chloroformate or t-butylchloroformate, or may be coupled directly using carbodiimides such as EDAC. For reaction with cysteine thiols on the enzyme, the hapten should contain a good leaving group such as I, Br or tosyl; alternatively, the hapten can contain a thiol, preferably activated with 2,2' dithiodipyridine, 5,5'dithiobis(2-nitrobenzoic acid) (DTNB), dithioerythritol (DTE), and the like.

Another method of conjugation, described in Rowley, G. L., D. Leung, and P. Singh (U.S. Pat. No. 4,220,722) involves modification of the enzyme with bromoacetyl containing reactants; the bromo groups are subsequently reacted with thiol-containing haptens. The reaction of enzyme with bromoacetyl modifier, and the bromoacetyl enzyme with the thiolated hapten, are subject to the same reaction condition variables described above.

Included within the above compounds of Formula I are compounds of the formula:

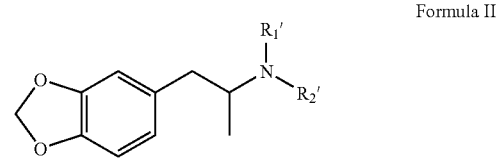

Formula II wherein:

$R^{1'}$ is H, lower alkyl or a protecting group, $R^{2'}$ is a protecting group, or (a) $-(CH_2)_aC(O)(CH_2)_bSR^{3'}$, wherein a is 0 to 5, 1 to 4, 1 to 3, 2 to 4, 1 to 2, typically 0, b is 1 to 5, 1 to 4, 1 to 3, 2 to 4, 1 to 2, typically 1, and $R^{3'}$ is H or lower alkyl or $(CH_2)_cC(O)NR^{4'}R^{5'}$ wherein $R^{4'}$ is H or lower alkyl and $R^{5'}$ is H, an immunogenic carrier or a label, or (b) $(A)_d(Q)_n$ wherein Q is H or $-(CH_2)_eCH(R^{8'})(CH_2)_fOC(O)(CH_2)_gR^{9'}$ being H only when d is 1 wherein A is $-C(O)(CH_2)_hC(O)N(R^{10})((CH_2)_jO(CH_2)_kO)_m(CH)_pNR^{11}-$, d is 0 or 1, n is 0 or 1 wherein one of d or n is 1, h is 1 to 5, 1 to 4, 1 to 3, 2 to 4, 1 to 2, typically 2, $R^{10}$ is H or lower alkyl, j is 1 to 5, 1 to 4, 1 to 3, 2 to 4, 1 to 2, typically 2, k is 1 to 5, 1 to 4, 1 to 3, 2 to 4, 1 to 2, typically 2, m is 1 to 3, 1 to 2, typically 1, $R^{11}$ is H or lower alkyl, e is 1 to 5, 1 to 4, 1 to 3, 2 to 4, 1 to 2, typically 1, $R^{8'}$ is OH or H, f is 1 to 5, 1 to 4, 1 to 3, 2 to 4, 1 to 2, typically 1, g is 0 to 5, 1 to 4, 1 to 3, 2 to 4, 1 to 2, typically 0, and $R^{9'}$ is H, an immunogenic carrier or a label, and including the acid salts thereof.

Specific embodiments of compounds of Formula II include:

A compound according to Formula II wherein $R^{1'}$ is H or lower alkyl and $R^{2'}$ is $-(CH_2)_aC(O)(CH_2)_bSR^3$ wherein a is 0, b is 1, $R^3$ is H.

A compound according to Formula II wherein $R^{1'}$ is H or lower alkyl and $R^{2'}$ is $-(CH_2)_aC(O)(CH_2)_bSR^{3'}$ wherein a is 0, b is 1, $R^{3'}$ is $(CH_2)_cC(O)NR^{4'}R^{5'}$ wherein c is 1, $R^{4'}$ is H and $R^{5'}$ is a poly(amino) acid.

A compound according to Formula II wherein $R^{1'}$ is H or lower alkyl and $R^{2'}$ is $(A)_d(Q)_n$ wherein d is 0, n is 1, Q is $-(CH_2)_eCH(R^{8'})(CH_2)_fOC(O)(CH_2)_gR^{9'}$, e is 1, $R^{8'}$ is OH, f is 1, g is 0 and $R^{9'}$ is a poly(amino) acid.

A compound according to Formula II wherein $R^{1'}$ is H or lower alkyl and $R^{2'}$ is $(A)_d(Q)_n$ wherein d is 0, n is 1, Q is H, A is $-C(O)(CH_2)_hC(O)NR^{10}((CH_2)_jO(CH_2)_kO)_m(CH)_2NR^{11}-$, $R^{10'}$ is H, h is 2, m is 1, j is 2, k is 2, $R^{10'}$ is H.

A compound according to Formula II wherein $R^{1'}$ is H or lower alkyl and $R^{2'}$ is $(A)_d(Q)_n$ wherein d is 1, n is 1, Q is $-(CH_2)_eCH(R^{8'})(CH_2)_fOC(O)(CH_2)_gR^{9'}$, e is 1, $R^{8'}$ is OH, f is 1, g is 0, A is $-C(O)(CH_2)_hC(O)NR^{10}((CH_2)_jO(CH_2)_kO)_m(CH)_2NR^{11}-$, $R^{10'}$ is H, h is 2, m is 1, j is 2, k is 2, $R^{10'}$ is H and $R^{9'}$ is a poly(amino) acid or a particle.

Also included within the above compounds of Formula I are compounds of the formula:

Formula III

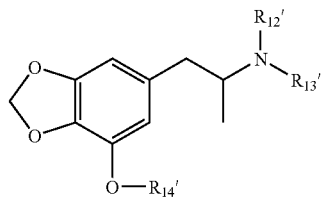

wherein:
$R^{12'}$ is H or lower alkyl,
$R^{13'}$ is H or lower alkyl,
$R^{14'}$ is a protecting group, or —$(CH_2)_rC(O)NR^{15'}(CH_2)_s(D)_tR^{16'}$, wherein r is 1 to 5, 1 to 4, 1 to 3, 2 to 4, 1 to 2, typically 1, $R^{15'}$ is H or lower alkyl, s is 1 to 5, 1 to 4, 1 to 3, 2 to 4, 1 to 2, typically 2, D is S, O or N, t is 0 or 1 being 0 when $R^{16'}$ is maleimidyl or succinimidyl, $R^{16'}$ is H, a protecting group, maleimidyl, succinimidyl, or —$(CH_2)_qC(O)NR^{17'}R^{18'}$, wherein q is 1 to 5, 1 to 4, 1 to 3, 2 to 4, 1 to 2, typically 1,
$R^{17'}$ is H, lower alkyl or a protecting group,
$R^{18'}$ is H, lower alkyl, a protecting group, an immunogenic carrier or label, and including the acid salts thereof.

Specific embodiments of compounds of Formula III include:

A compound according to Formula III wherein $R^{12'}$ is H and $R^{13'}$ is H or lower alkyl, $R^{14'}$ is —$(CH_2)_rC(O)NR^{15'}(CH_2)_s(D)_tR^{16'}$, wherein r is 1, $R^{15'}$ is H, s is 2, D is S, t is 1 and $R^{16'}$ is H.

A compound according to Formula III wherein $R^{12'}$ is H and $R^{13'}$ is H or lower alkyl, $R^{14'}$ is —$(CH_2)_rC(O)NR^{15'}(CH_2)_s(D)_tR^{16'}$, wherein r is 1, $R^{15'}$ is H, s is 2, t is 0 and $R^{16'}$ is succinimidyl or maleimidyl.

A compound according to Formula III wherein $R^{12'}$ is H and $R^{13'}$ is H or lower alkyl, $R^{14'}$ is —$(CH_2)_rC(O)NR^{15'}(CH_2)_s(D)_tR^{16'}$, wherein r is 1, $R^{15'}$ is H, s is 2, D is S, t is 1 and $R^{16'}$ is —$(CH_2)_qC(O)NR^{17'}R^{18'}$, q is 1, $R^{17'}$ is H and $R^{18'}$ is a poly(amino) acid or a particle.

Another embodiment is a compound of the formula:

Formula IV

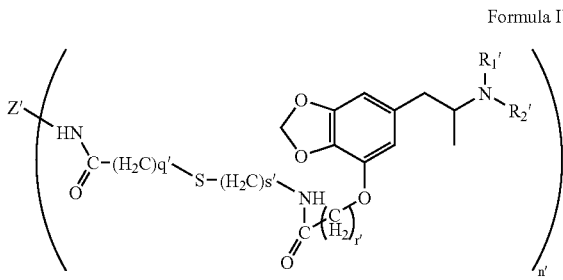

wherein:
$R^{1'}$ is H, lower alkyl or a protecting group,
$R^{2'}$ is H, lower alkyl or a protecting group,
r' is 1 to 5,
s' is 1 to 5,
q' is 1 to 5,
Z' is an enzyme, for example, G6PDH,
n' is an integer between 1 and the molecular weight of said enzyme divided by about 500.

Another embodiment is a compound of the formula:

Formula V

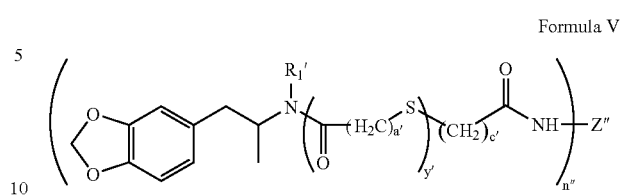

wherein:
$R^{1'}$ is H, lower alkyl or a protecting group,
$R^{2'}$ is H, lower alkyl or a protecting group,
a' is 1 to 5,
y' is 0 or 1, usually 1,
Z" an enzyme, for example, G6PDH,
c' is 1 to 5,
n" is an integer between 1 and the molecular weight of said enzyme divided by about 500.

Another embodiment is a compound of the formula:

Formula VI wherein:
$R^{1'}$ is H or lower alkyl, typically H or methyl or ethyl,
$R^{2'}$ is H or lower alkyl, typically H or methyl or ethyl,
r' is 1 to 5,
s' is 1 to 5,
q' is 1 to 5,
Z' is an immunogenic protein or a non-poly(amino acid) immunogenic carrier,
n' is an integer between 1 and the molecular weight of said immunogenic protein or said immunogenic carrier divided by about 500.

Another embodiment is a compound of the formula:

Formula VII

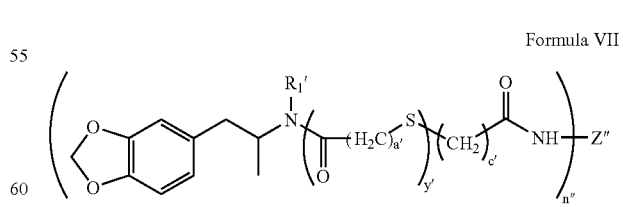

wherein:
$R^{1'}$ is H or lower alkyl, typically, H or methyl or ethyl,
a' is 1 to 5,
y' is 0 or 1, usually 1, Z" is an immunogenic protein or a non-poly(amino acid) immunogenic carrier, c' is 1 to 5, n" is an integer between 1 and the molecular weight of said immunogenic protein or said immunogenic carrier divided by about 500.

Synthesis

The syntheses of representative examples of the above compounds are discussed herein by way of illustration and not limitation. Other synthetic procedures will be suggested to those skilled in the art in view of the disclosure herein. Other compounds within the scope of the present invention may be prepared using suitable variants of the reagents employed below. The reaction temperatures and time are those customary for the type of reactions conducted and should be evident to those skilled in the art.

Figure 5:
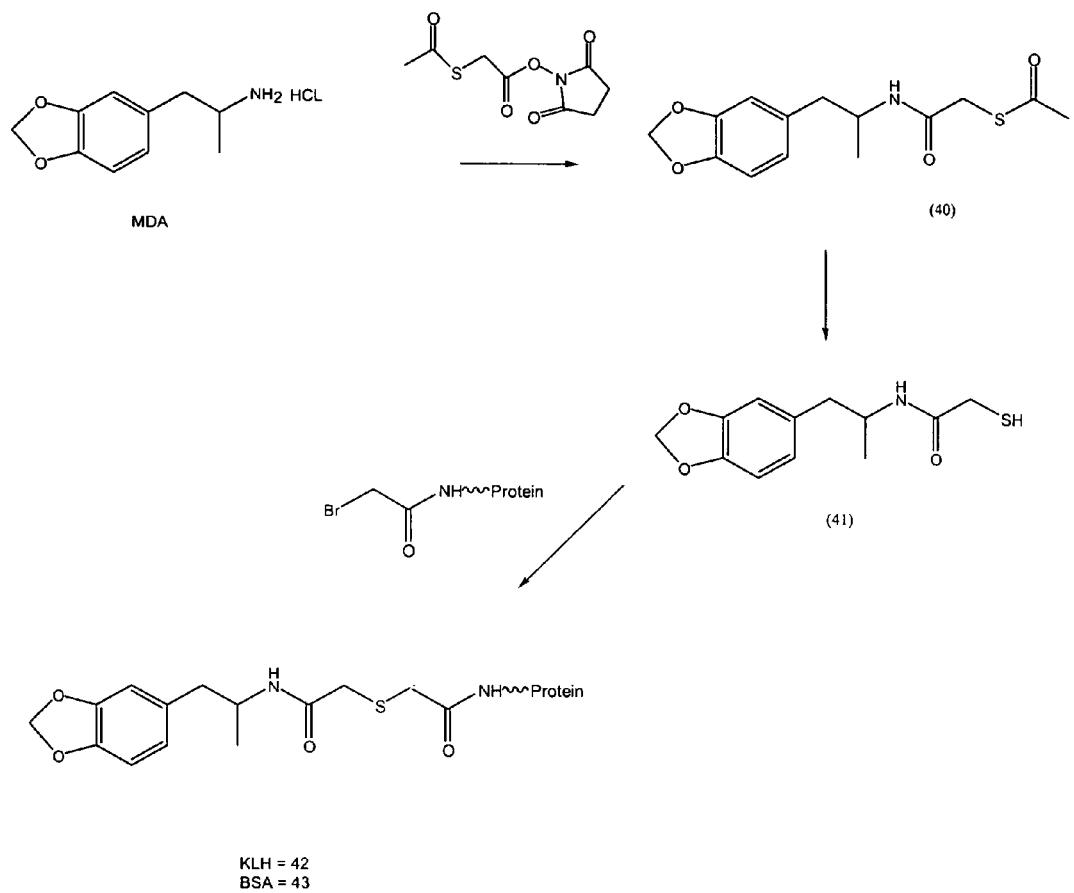
FIG. 5 is a reaction scheme depicting an example of a synthesis of MDA hapten (41), MDA-KLH immunogen (42) or MDA-BSA immunogen (43).
Figure 6:
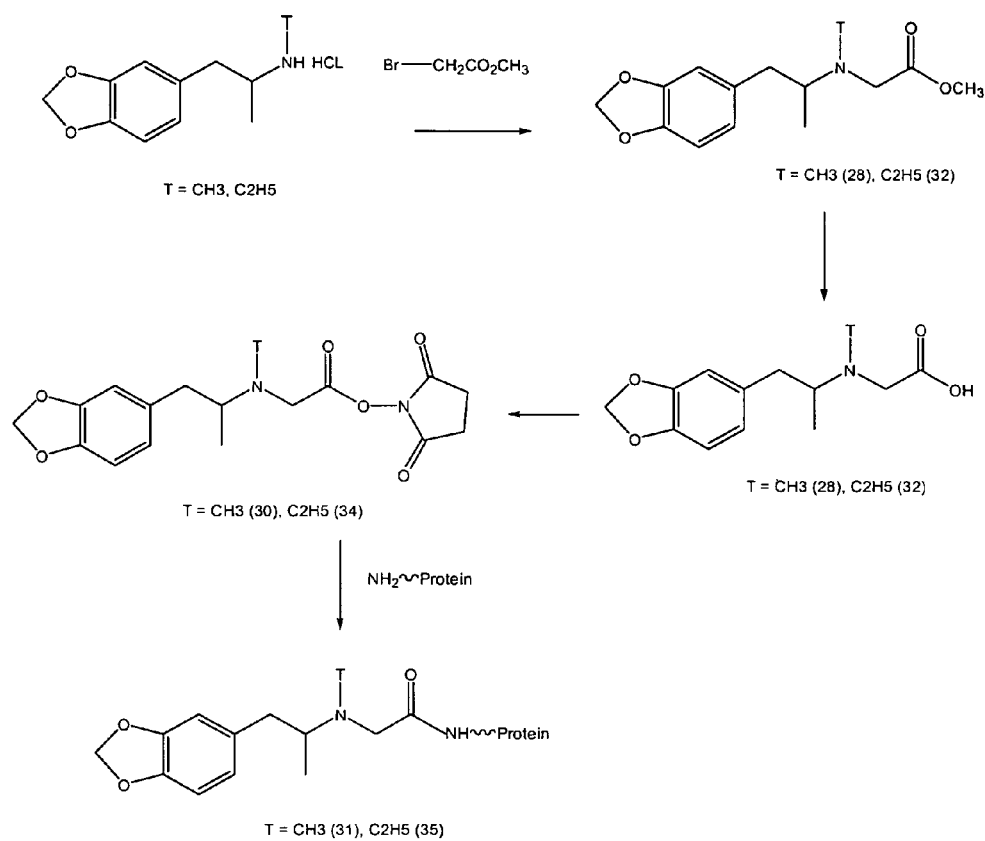
FIG. 6 is a reaction scheme depicting an example of a synthesis of MDMA-BSA immunogen (31) or MDEA-BSA immunogen (35).
Figure 7:
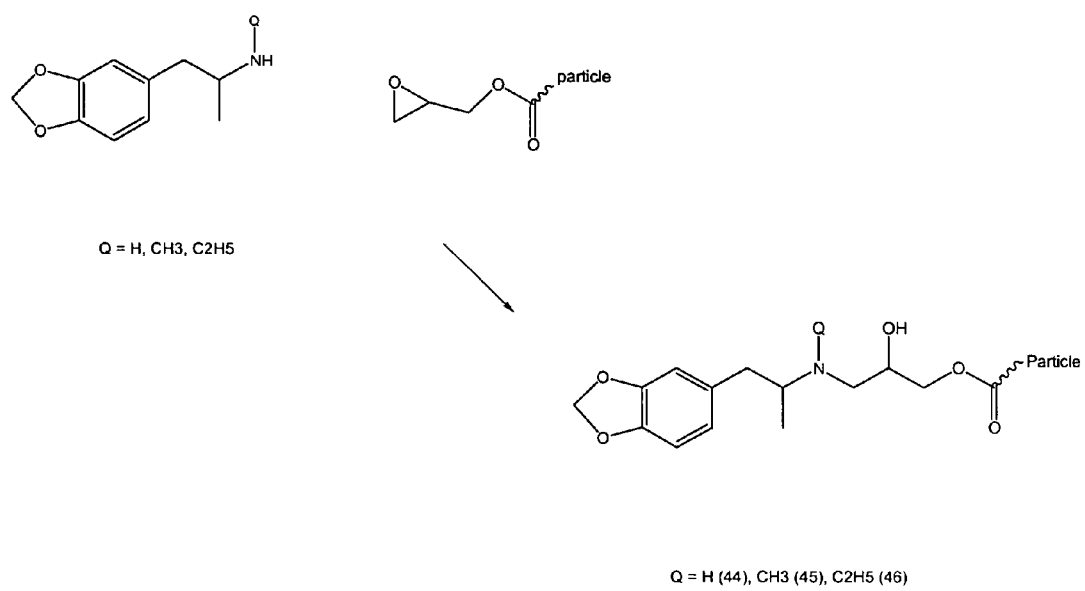
FIG. 7 is a reaction scheme depicting an example of a synthesis of MDA particle reagent (44), MDMA particle reagent (45) and MDEA particle reagent (46).

Two approaches are discussed hereinbelow, by way of illustration and not limitation, for synthesizing seven compounds 10, 22, 27, 29, 33, 37 and 41 and their immunogens. In one approach, a linker is introduced on the benzene ring of MDA and MDMA molecules (FIGS. 1–4). In the other approach, the amine nitrogen of the above molecules is modified (FIGS. 5–7).

Referring to FIG. 1, the synthesis of 10 commenced with a condensation of commercially available starting material 1 with nitroethane in a buffered acidic medium such as, for example, ammonium acetate and acetic acid to give the nitro compound 2. The nitro group of compound 2 is reduced using a suitable reducing agent such as, for example, lithium aluminum hydride, aluminum borohydride, etc., in an organic medium such as, for example, an aromatic hydrocarbon, an ether (e.g., ethyl ether, THF, etc.), a formamide (e.g., dimethylformamide), and so forth and combinations thereof, e.g., ether/toluene to give amine 3. The amine group of 3 is protected with a protecting group such as, for example, trifluoroacetic anhydride and the like in a suitable solvent such as methylene dichloride, an ether (e.g., THF), and so forth in the presence of a base such as an alkyl amine, for example, ethyl amine to generate compound (4). Compound (4) is a building block designed for the synthesis of MDA, MDEA and MDMA haptens. Selective deprotection of the methyl group of 4 with a deprotection agent such as trimethylsilyl iodide under basic conditions, e.g., an aromatic amine such as pyridine, quinoline, and the like, yields phenol (5). Protection (alkylation) of the resulting phenol 5 is carried out using a protecting agent such as, for example, tert-butylbromoacetate (t-Boc), under basic conditions to give compound (6). Suitable bases include metal hydrides such as, e.g., NaH, $CaH_2$, etc., sodium carbonate, potassium carbonate, and the like, in an organic solvent such as, for example, dimethylformamide (DMF), organic ethers, e.g., ethyl ether, tetrahydrofuran (THF), dioxane, and the like. Reaction of 6 with a deprotection agent to selectively remove the t-Boc protecting group gave acid (7). Such deprotection agents include, for example, an organic acid (e.g., trifluoroacetic acid and the like), an inorganic acid (e.g., HCl and the like), and so forth. Acid (7) is activated by an appropriate activating agent such as, for example, dicyclohexylcarbodiimide (DCC) and N-hydroxysuccinic acid ester (NHS), EDAC, and so forth, followed by reaction with amine ($H_2NCH_2CH_2SSCH_3$) to give disulfide compound (8). Deprotection of the amine group of compound (8) is carried out under basic conditions in an organic solvent such as, for example, a carbonate, e.g., potassium carbonate in an alcohol such as, e.g. methanol, ethanol and the like. The disulfide bond of 9 is cleaved to give the desired MDA hapten, thiol 10. Cleaving conditions include, for example, DTE, DTNB, TCEP-HCl, and an alkyl amine, e.g., ethyl amine, in an organic solvent such as, e.g., an alcohol, an ether, and combinations thereof.

Figure 2:
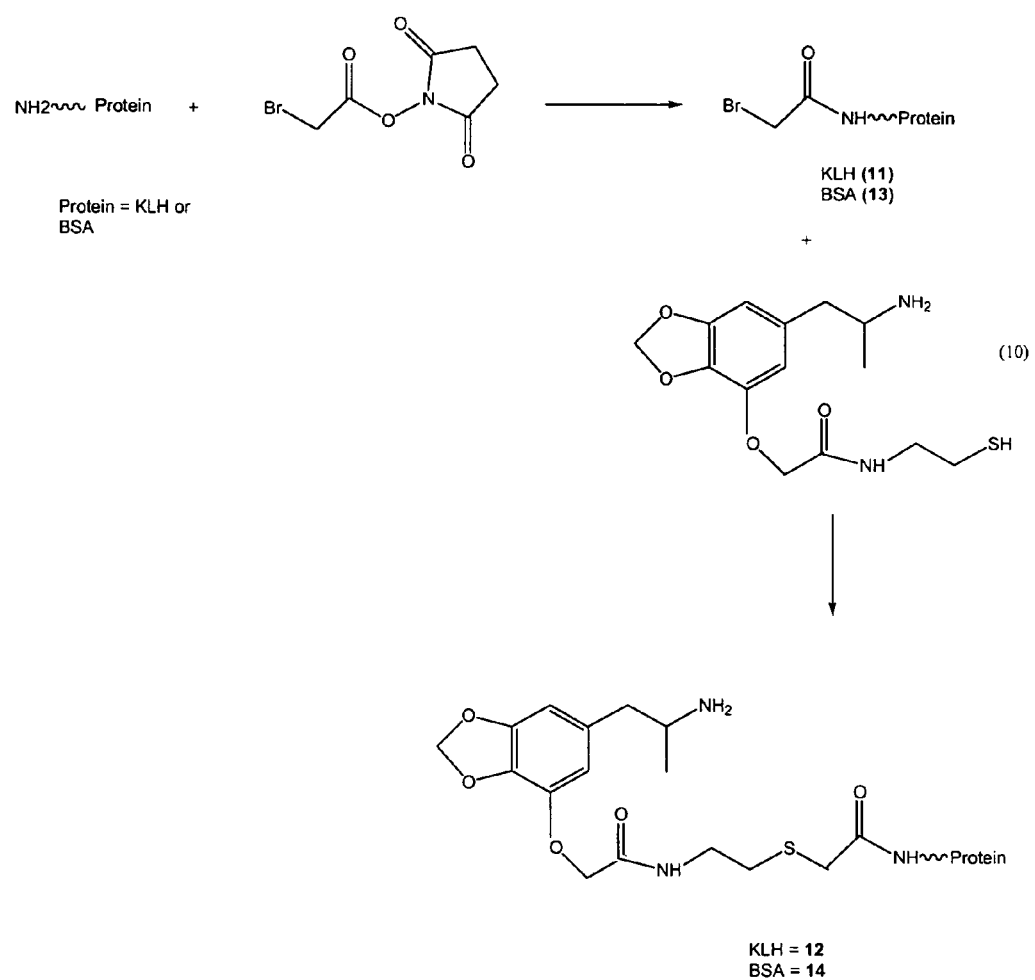
FIG. 2 is a reaction scheme depicting an example of a synthesis of MDA-KLH immunogen (12) or MDA-BSA immunogen (14).

Referring to FIG. 2, the amine group of a protein such as, for example, KLH, BSA, and the like is treated with succinimidylbromo-acetate to introduce the bromo-acetamide functional group for thiol modification giving modified KLH (11) and modified BSA (13). Reaction conditions include, for example, a buffer solution at pH of about 7 to 9, about 7.5 to 8.5, about 8. Such buffer solutions include, for example, a phosphate buffer, e.g., a dihydrogen phosphate, a hydrogen phosphate, etc., and combinations thereof. Reaction of thiol (10) (see FIG. 1) with modified protein KLH 11 and modified protein BSA 13, gives the desired immunogens [KLH immunogen (12) and BSA immunogen (14)]. Reaction conditions include, for example, a buffer solution at pH of about 7 to 9, about 7.5 to 8.5, about 8. Such buffer solutions include, for example, phosphate buffer, e.g., a dihydrogen phosphate, a hydrogen phosphate, etc., and combinations thereof. The resulting immunogens may be purified by appropriate purification techniques such as, for example, column chromatography, e.g., SEPHADEX, etc., and the like using a suitable eluent, e.g., phosphate buffer, etc. The attachment of a protein to the linking moiety of the molecule is usually by way of amino groups on a protein, where the nitrogen of the amino group may be the nitrogen of the linking group depicted above.

Figure 3:
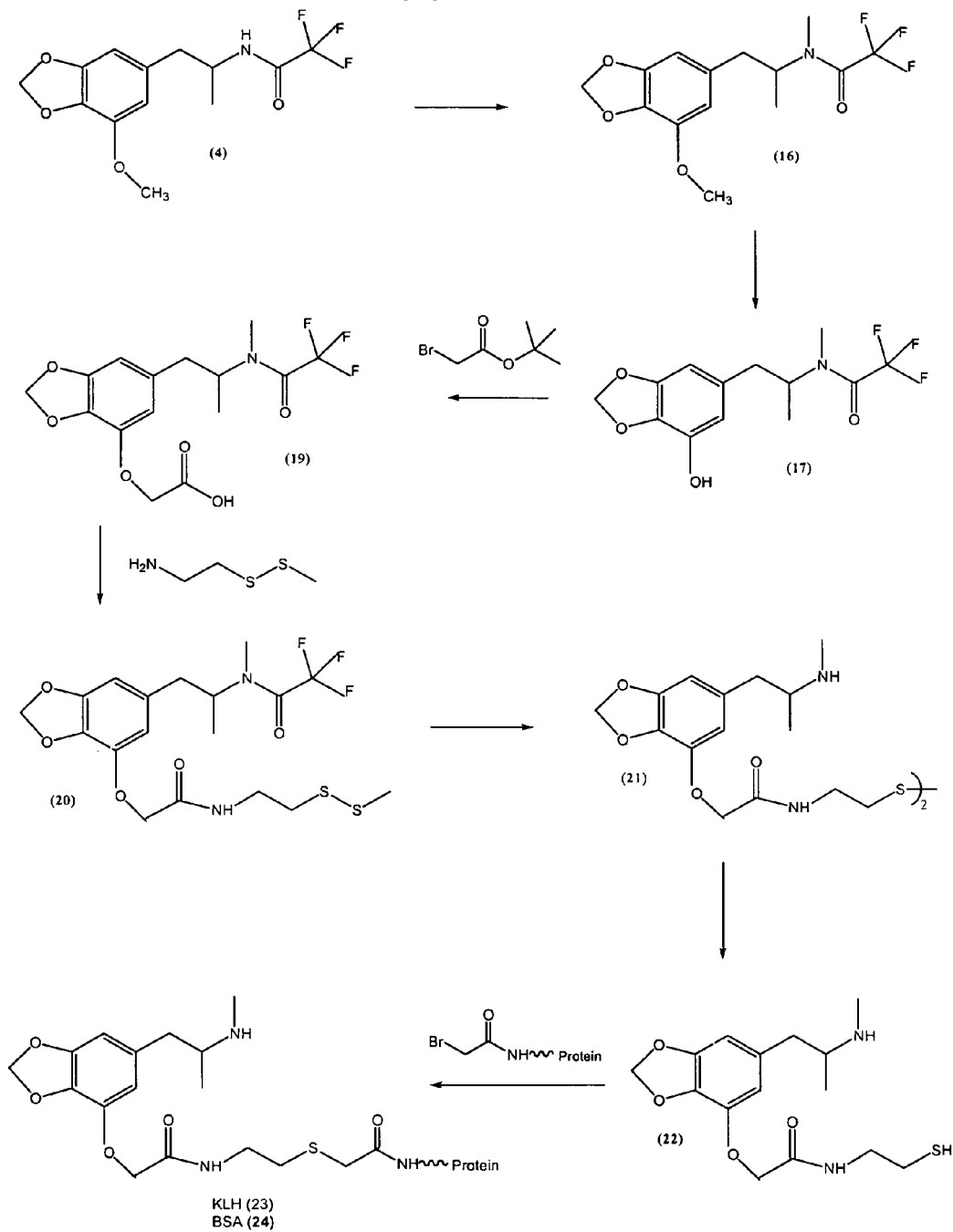
FIG. 3 is a reaction scheme depicting an example of a synthesis of MDMA-KLH immunogen (23) or MDMA-BSA immunogen (24).

Referring to FIG. 3, the synthesis of MDMA hapten (22) starts with alkylation of the secondary amine group of compound (4) with an alkylation agent such as, for example, methyl iodide, and the like under basic conditions such as an inorganic base, e.g., potassium hydride, sodium hydride, calcium hydride, and the like in an organic solvent such as an ether, e.g., tetrahydrofuran, 18-crown-6, and so forth and combinations thereof. Selective removal of the methoxyl group of 16 gave phenol (17). Selective removal agents include, for example, trimethylsilyl iodide under basic conditions, e.g., an aromatic amine such as pyridine, quinoline, and the like. Reaction of 17 with a protecting group such as, e.g., t-Boc bromoacetate under basic conditions, which include, for example, an inorganic base such as, e.g., potassium carbonate and the like in an organic solvent such as, for example, an ether, e.g., tetrahydrofuran and so forth yields the protected compound. The t-Boc group is removed by treatment with a removal agent such as, for example, an organic acid, e.g., trifluoroacetic acid in an organic solvent such as, for example, a chlorinated hydrocarbon, e.g., methylene dichloride to give acid (19). Acid (19) is activated by an appropriate activating agent such as, for example, dicyclohexylcarbodiimide (DCC) and N-hydroxysuccinic acid ester (NHS), EDAC and so forth, followed by reaction with amine $H_2NCH_2CH_2SSCH_3$ to give disulfide compound (20). Removing the amine protecting group of 20 and then cleaving the disulfide bond of 21 followed by reaction with the resulting thiol 22 with bromoacetamide of the protein gave the desired MDMA-KLH (23) and MDMA-BSA (24). Deprotection of the amine group of compound (20) is carried out under basic conditions in an organic solvent such as, for example, a carbonate, e.g., potassium carbonate in an alcohol such as, e.g. methanol, ethanol and the like. The disulfide bond of 21 is cleaved to give the desired MDMA hapten, thiol (22). Cleaving conditions include, for example, an alkyl amine, e.g., ethyl amine, in an organic solvent such as, e.g., an alcohol, an ether, and combinations thereof. Reaction of thiol (22) with the appropriate modified protein KLH and modified protein BSA, gives the desired immunogens (23) and (24). Reaction conditions include, for example, a buffer solution at pH of about 7–9, about 7.5–8.5, about 8. Such buffer solutions include, for example, a phosphate buffer, e.g., a dihydrogen phosphate, a hydrogen phosphate, and combinations thereof. Thiol (22) is also employed in the synthesis of glucose-6-phosphate dehydrogenase (G6PDH) conjugates, which are enzyme conjugates useful in assays for detection of the ecstasy compounds.

Figure 4:
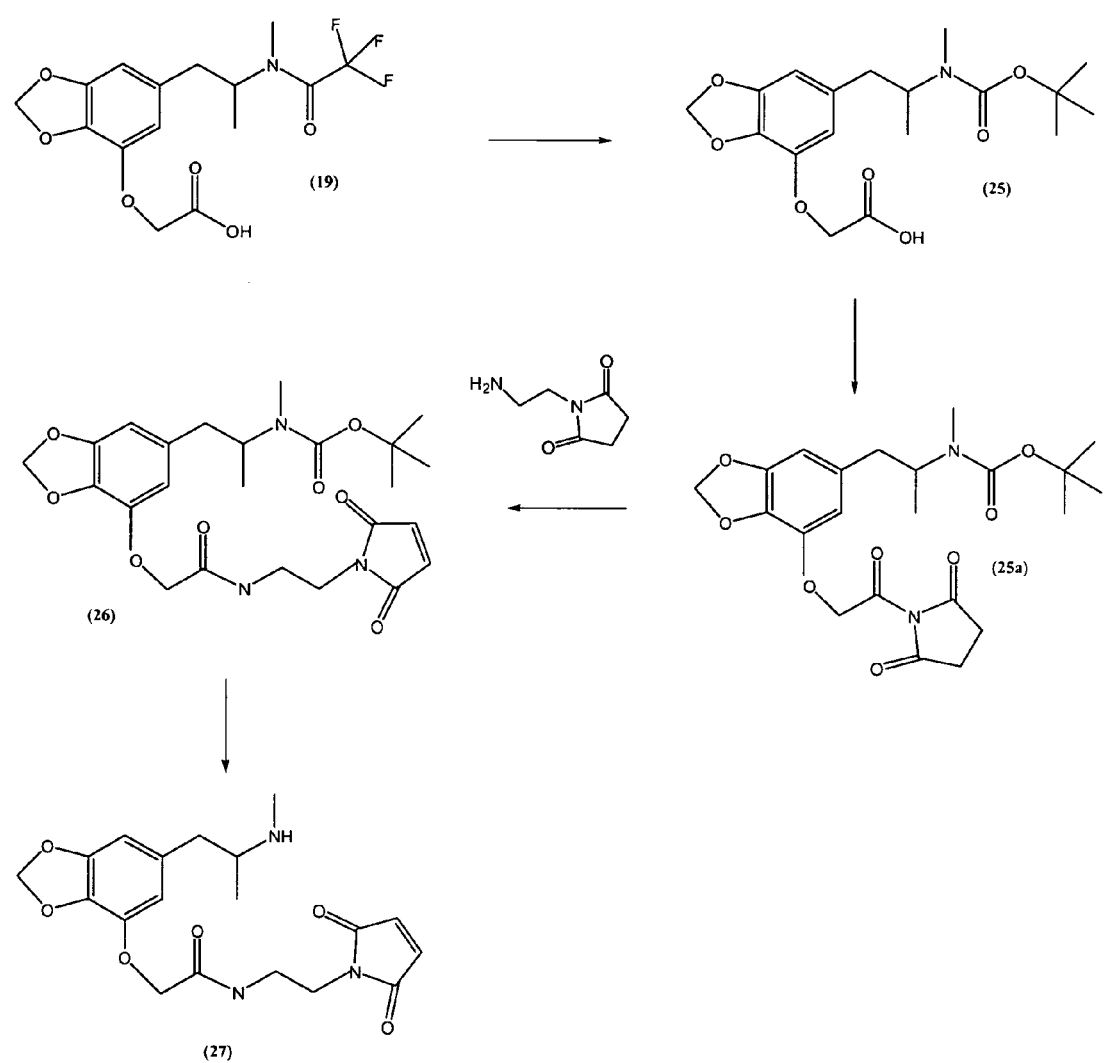
FIG. 4 is a reaction scheme depicting an example of a synthesis of MDMA hapten (27).

Referring to FIG. 4, synthesis of MDMA hapten (27) starts with the reaction of intermediate compound (19) to give protected amine (25). A suitable protection agent such as, for example, an agent for introducing a t-Boc protecting group, e.g., di-tert-butyldicarbonate (t-Boc)$_2$O, is employed under basic conditions such as, for example, an inorganic base, e.g., potassium carbonate and the like in an organic solvent such as, for example, an alcohol, e.g., methanol, ethanol and so forth. The acid group of 25 is activated by an appropriate activating agent such as, for example, dicyclohexylcarbodiimide (DCC) and N-hydroxysuccinic acid ester (NHS), EDAC, and so forth in a suitable organic solvent such as, for example, an ether, e.g. tetrahydrofuran, and so forth. The activated compound (25a) is subsequently reacted with maleimidoethyl amine to give compound (26) under conditions that include an organic solvent and the like. Removal of the t-Boc protection group by treatment of compound (26) with a removal agent such as, for example, trifluoroacetic acid in an organic solvent such as, for example, a chlorinated hydrocarbon, e.g., methylene dichloride, gives the final product (27).

Referring to FIG. 5, reaction of MDA hydrochloride with 2-mercapto[S-acetyl]acetic acid N-hydroxysuccinimide ester gives compound (40). The reaction is conducted in an organic solvent such as, for example, an ether, e.g., tetrahydrofuran, and the like in the presence of an organic base such as a mono-, di-, and tri-alkyl amine, for example, diisopropyl ethyl amine (DIPEA). Other suitable bases include ethyl amine, diethyl amine, triethyl amine and so forth. Compound (40) is hydrolyzed under basic conditions to free thiol (41). The basic conditions are, for example, an inorganic base, e.g., a carbonate, e.g., potassium carbonate, sodium carbonate, and the like in an organic solvent such as, for example, an alcohol, e.g., methanol, ethanol and so forth. Chemistry similar to that described with regard to FIG. 2 was applied to prepare the KLH (42) and BSA (43) immunogens by using hapten (41).

Referring to FIG. 6 reaction of MDMA with methyl bromoacetate under basic conditions gave compound (28). Suitable bases include metal hydrides such as, e.g., NaH, CaH$_2$, etc., sodium carbonate, potassium carbonate, and the like, in an organic solvent such as, for example, dimethylformamide (DMF), organic ethers, e.g., ethyl ether, tetrahydrofuran (THF), dioxane, and the like. Hydrolysis of 28 followed by activation of the resulting acid (29) with a suitable activation agent such as, for example, EDAC, NHS and the like gave the desired intermediate (30). Hydrolysis may be carried out, for example, using an inorganic base such as, for example, a metal hydroxide, e.g., sodium hydroxide, potassium hydroxide, and the like in an oxygenated organic solvent such as, for example, an alcohol, e.g., methanol, ethanol, and so forth. Reaction of 30 with BSA in a buffered solution such as a phosphate buffer, e.g., sodium phosphate, potassium phosphate, and so forth (e.g., 0.1 M, pH=8.0) gave the conjugated immunogen (31). The concentration of protein was measured by BCA Protein Concentration Assay and the TNBS method was used for hapten number determination. The conjugate had a concentration of 1.74 mg/mL with a hapten number of 40, and was used for antibody production. In a similar way, an MDEA immunogen (35) was prepared. The MDEA-BSA had a protein concentration of 2.11 mg/ml with a hapten number of 43 and was utilized for antibody production.

The following discussion relates to the synthesis of latex particles for use in an ecstasy PETINIA assay. The nitrogen atom of the MDA, MDMA or MDEA molecule is employed for attachment to the particles. Referring to FIG. 7, MDA hydrochloride (Q=H) or MDMA hydrochloride (Q=CH$_3$) or MDEA hydrochloride (Q=C$_2$H$_5$) may be employed as the starting molecule in the synthesis. The starting material is combined with a particle reagent that is an ester formed from a carboxylic acid functionality on the particle and 1,2-epoxy-3-hydroxypropane. The resulting product is a particle to which is attached an MDA moiety (compound 44), an MDMA moiety (compound 45) or an MDEA moiety (compound 46).

Figure 8:
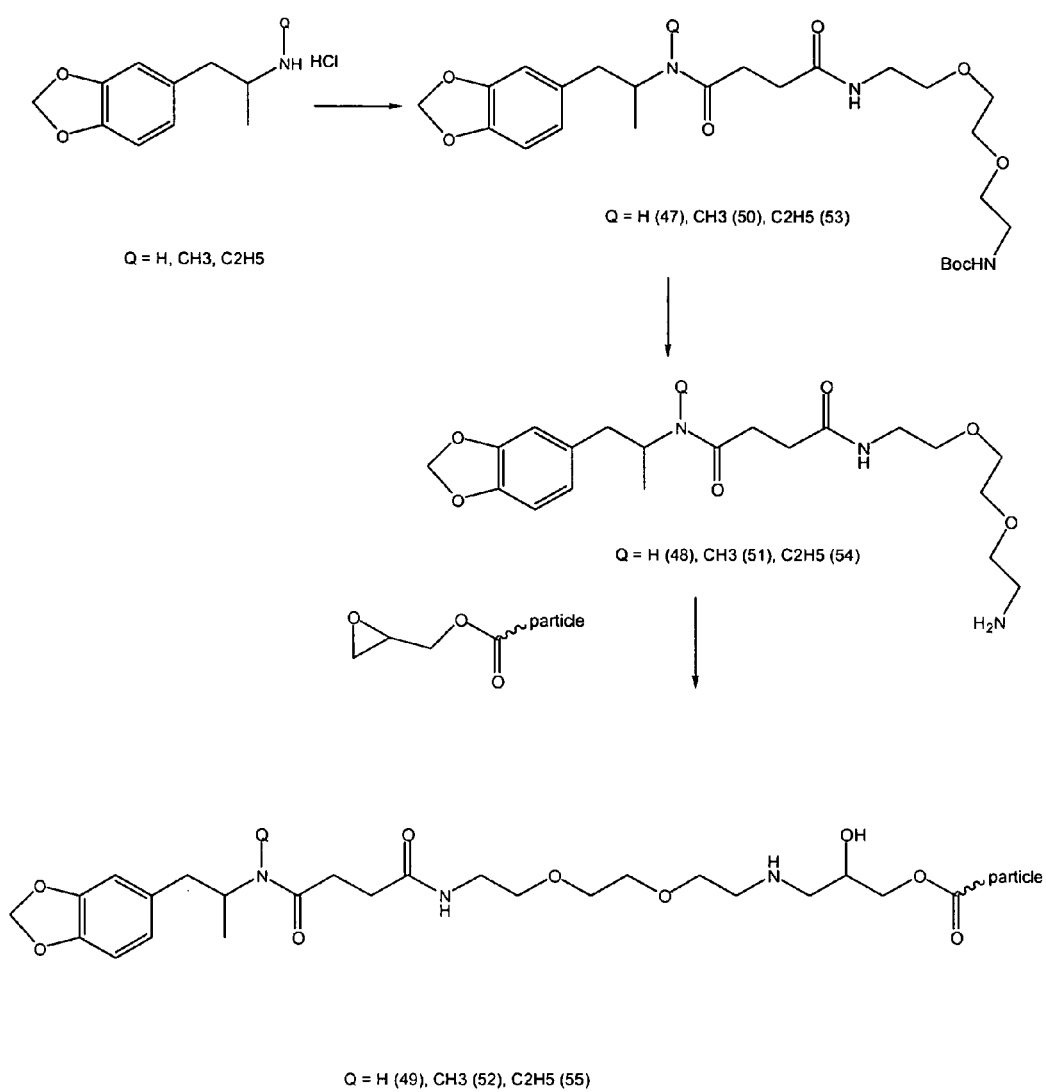
FIG. 8 is a reaction scheme depicting an example of a synthesis of MDA particle reagent (49), MDMA particle reagent (52) and MDEA particle reagent (55).

Referring to FIG. 8, MDA hydrochloride or MDMA hydrochloride or MDEA hydrochloride may be employed as the starting molecule in the synthesis. The amine functionality of the starting material is protected to give compound 47 (Q=H), 50 (Q=CH$_3$) or 53 (Q=C$_2$H$_5$) by treating the starting material with a suitable protection agent such as, for example, an agent for introducing a t-Boc protecting group, e.g., Boc-C14. The reaction is carried out under basic conditions such as, for example, an organic base such as a mono-, di-, and tri-alkyl amine, for example, triethyl amine (TEA). Other suitable bases include ethyl amine, diethyl amine, DIPEA amine and the like. The reaction is conducted in an organic solvent such as, for example, an alcohol, e.g., methanol, ethanol and so forth in the presence of, for example, N,N'-disuccinimidyl carbonate (DSC). Removal of the t-Boc protection group by treatment of compound (47, 50 or 53) with a removal agent such as, for example, an acid, e.g., trifluoroacetic acid in an organic solvent such as, for example, a chlorinated hydrocarbon, e.g., methylene dichloride, gives the compound (48) (Q=H), (Q=CH$_3$) (51) or (Q=C$_2$H$_5$) (54). Particles with compound 48, 51 or 54 attached may be prepared by reacting the respective compound with a particle reagent that has an 1,2-epoxy-3-hydroxypropane functionality. The reaction conditions are discussed above with respect to FIG. 8. The resulting product is a particle to which is attached an MDA moiety (compound 49), an MDMA moiety (compound 52) or an MDEA moiety (compound 55).

Assays

The assays of the present invention usually involve reactions between binding partners such as an ecstasy analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme—substrate, nucleic acid duplexes, IgG-protein A, polynucleotide pairs such as DNA—DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

The immunogens prepared in accordance with the present invention may be employed to prepare antibodies specific for a respective ecstasy analyte mentioned above. An antibody is an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector, which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

An analyte analog is a modified analyte, which can compete with the analogous analyte for a receptor, the modification providing means to join an analyte analog to another molecule. The analyte analog will usually differ from the analyte by more than replacement of a hydrogen with a bond that links the analyte analog to a hub or label, but need not. The analyte analog can bind to the receptor in a manner similar to the analyte. The analog may be, for example, a label conjugate of the analyte, an antibody directed against the idiotype of an antibody to the analyte and the like.

As indicated above, analyte analogs include label conjugates, which may be prepared from certain of the haptens described above by incorporation of a desired label. The two components may be bound together, optionally through a linking group, to form a single structure. The binding can be either covalent attachment such as by a direct connection, e.g., a chemical bond, between the components or between the components and a linking group or non-covalent attachment involving specific binding between complementary specific binding pair (sbp) members that are attached to components. The procedures employed for the conjugation are well-known in the art.

Typically, for covalent attachment, one or more of the components contains a functional group suitable for attachment to one or more of the other components. The functional groups suitable for attaching the components may be carbonyl functionalities, both oxocarbonyl, e.g., aldehyde, and non-oxocarbonyl (including nitrogen and sulfur analogs) e.g., carboxy, amidine, amidate, thiocarboxy and thionocarboxy. Alternative functionalities of oxo include active halogen, diazo, mercapto, olefin, particularly activated olefin, amino, phosphoro and the like. Of particular interest are activated esters or alkylating agents. Details of techniques for attaching molecules to one another are well known in the art. See, for example, Matthews, et al., *Anal. Biochem.* (1985) 151:205–209; Engelhardt, et al., European Patent Application No. 0302175 and U.S. Pat. No. 3,817,837, the relevant disclosure of which is incorporated herein by reference in its entirety.

As indicated above, the components, i.e., hapten and label, of the reagents may be attached together non-covalently. For example, a small organic molecule such as, for example, biotin including bis-biotin, fluorescein or the like may be incorporated into one of the components and the other component may be linked to a binding partner for the small organic molecule such as, for example, respectively, streptavidin, anti-fluorescein or the like. The binding of the binding partners results in the non-covalent attachment of the components to one another.

The aforementioned reagents may be employed in all types of immunoassays to determine the presence and/or amount of ecstasy analytes in a sample suspected of containing such analytes. The immunoassays may involve labeled or non-labeled reagents. Immunoassays involving non-labeled reagents usually comprise the formation of relatively large antigen-antibody complexes. Such assays include, for example, immunoprecipitin and agglutination methods and corresponding light scattering techniques such as, e.g., nephelometry and turbidimetry, for the detection of antigen-antibody complexes. Labeled immunoassays include enzyme immunoassays, fluorescence polarization inimunoassays, radioimmunoassay, inhibition assay, luminescent oxygen channeling assay, and so forth.

One general group of immunoassays include immunoassays of antigens or haptens using labeled analyte with a limited concentration of antibody. Another group of immunoassays involves the use of an excess of all of the principal reagents. Such assays include two-site sandwich assays, e.g., immunoradiometric assays, immunofluorometric assays, immunochemiluminometric assays, ELISA assays, and so forth. Another group of immunoassays includes precipitation, nephelometric and turbidimetric immunoassays, particle agglutination immunoassays, particle counting immunoassays, and the like. Another group of immunoassays are separation-free homogeneous assays in which the labeled reagents modulate the label signal upon antigen-antibody binding reactions. Another group of assays includes labeled antibody reagent limited competitive assays for hapten or antigen that avoid the use of problematic labeled antigens or haptens. In this type of assay, it is important that the solid phase immobilized analyte be present in a constant, limited amount. The partition of a label between the immobilized analyte and free analyte depends on the concentration of analyte in the sample.

The aforementioned haptens, label conjugates and antibodies may be employed to conduct an immunoassay for the ecstasy analytes MDA, MDMA, and/or MDEA. The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817, 837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285–288; the substrate labeled fluorescence immunoassay ("SLFIA") disclosed by Oellerich, J. Clin. Chem. Clin. Biochem. (1984) 22:895–904; the combined enzyme donor immunoassays ("CEDIA") disclosed by Khanna, et al., Clin. Chem. Acta (1989) 185:231–240; homogeneous particle labeled immunoassays such as particle enhanced turbidimetric inhibition immunoassays ("PETINIA"), particle enhanced turbidimetric immunoassay ("PETIA"), etc.; and the like.

Exemplary of heterogeneous assays are the enzyme linked immunosorbant assay ("ELISA") discussed in Maggio, E. T. supra; the radioimmunoassay, disclosed in Yalow, et al., J. Clin. Invest. 39:1157 (1960) and so forth.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of an antigen or hapten. Such assays include, for example, optical immunosensor assays, acoustic immunosensor assays, semiconductor immunosensor assays, electrochemical transducer immunosensor assays, potentiometric immunosensor assays, amperometric electrode assays, and the like.

The above reagents may also be employed in multi-analyte immunoassays where one or more entactogen analytes may be the subject of detection along with one or more other analytes such as other drugs of abuse and the like. Such multi-analyte systems are described in U.S. Pat. No. 5,135,836, the relevant portions of which are incorporated herein by reference.

The homogeneous or heterogeneous assays, particularly enzyme immunoassays and fluorescence polarization immunoassays, are normally carried out in an aqueous buffered medium at a moderate pH, generally that which provides optimum assay sensitivity. The aqueous medium may be solely water or may include from 0 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the method in accordance with the present invention. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

One or more incubation periods may be applied to the medium at one or more intervals including any intervals between addition of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 6 hours, usually, from about 2 seconds to about 1 hour, more usually, about 1 to about 5 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., more usually from about 15 to about 40° C.

The concentration of ecstasy analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte will normally determine the concentrations of the various reagents.

The concentration of analytes to be detected will generally vary from about $10^{-5}$ to about $10^{-17}$ M, more usually from about $10^{-6}$ to about $10^{-14}$ M. In general, a predetermined cut-off level is established for each analyte suspected of being in a sample. The particular predetermined cut-off level generally is determined on an analyte by analyte basis. Those skilled in the art are well aware of the factors relating to the selection of predetermined cut-off levels. For example, for many drugs of abuse, the cut-off levels are determined by SAMSA, an agency of the Department of Health and Human Services. The nature of the signal producing system may be a consideration in determining the predetermined cut-off levels of some analytes. Another consideration is that the expected variation in concentration of the analytes that is of significance should provide an accurately measurable signal difference.

The concentrations of the various reagents in the assay medium will generally be determined by the concentration range of interest of the entactogen analyte. However, the final concentration of each of the reagents will normally be determined empirically to optimize the sensitivity of the assay over the range. That is, a variation in concentration of entactogen analyte that is of significance should provide an accurately measurable signal difference. Considerations such as the nature of the signal producing system and the nature of, and predetermined cut-off levels for, the entactogen analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from about 30 seconds to about 6 hours, more usually from about 1 minute to about 1 hour.

The following examples further describe the specific embodiments of the invention by way of illustration and not limitation and are intended to describe and not to limit the scope of the invention.

In a homogeneous assay after all of the reagents have been combined, the signal is determined and related to the amount of ecstasy analyte in the sample. For example, in an EMIT assay for MDA, a sample suspected of containing MDA is combined in an aqueous medium either simultaneously or sequentially with an MDA-enzyme conjugate and antibody capable of recognizing MDA and the conjugate, both of which are prepared in accordance with the present invention. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The MDA and the MDA-enzyme conjugate compete for binding sites on the antibody. The enzyme activity in the medium is then determined, usually by spectrophotometric means, and is compared to the enzyme activity determined when calibrators or reference samples are tested in which a known amount of MDA is present. Typically, the calibrators are tested in a manner similar to the testing of the sample suspected of containing MDA. The calibrators will typically contain differing, but known, concentrations of the MDA analyte to be determined. Preferably, the concentration ranges present in the calibrators will span the range of suspected MDA concentrations in the unknown samples.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In a typical competitive assay a support having an antibody for an ecstasy analyte such as, for example, an antibody for MDA, bound thereto is contacted with a medium containing the sample and an MDA-label conjugate where MDA is conjugated to a detectable label such as an enzyme. After separating the support and the medium, the label activity of the support or the medium is determined by conventional techniques and related to the amount of MDA in the sample.

The support may be comprised of an organic or inorganic, solid or fluid, water insoluble material, which may be transparent or partially transparent. The support can have any of a number of shapes, such as particle, including bead, film, membrane, tube, well, strip, rod, plate and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

Binding of components to the surface of a support may be direct or indirect, covalent or non-covalent and can be accomplished by well-known techniques, commonly available in the literature, as discussed above. See, for example, "Immobilized Enzymes," Ichiro Chibata, Halsted Press, New York (1978) and Cautrecasas, *J. Biol. Chem.*, 245:3059 (1970). The surface of the support is usually polyfunctional or be capable of being polyfunctionalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above).

Binding of the antibody for MDA and MDA results in the formation of an immune complex that can be detected directly or indirectly in numerous ways that are well known in the art. The immune complexes are detected directly, for example, when the antibodies employed are conjugated to a label. The immune complex is detected indirectly by examining for the effect of immune complex formation in an assay medium on a signal producing system or by employing a labeled receptor that specifically binds to an antibody produced by employing one of the hapten immunogen conjugates of the invention.

Activation of the signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems no agent for activation is necessary such as those systems that involve a label that is a radioactive label, an enzyme, and so forth. For enzyme systems addition of a substrate and/or a cofactor may be necessary.

In certain embodiments first and second labels may be employed and comprise a label pair. These label pairs may be, for example, a singlet oxygen generator or sensitizer and chemiluminescent reactant pair, an enzyme pair wherein a product of the first enzyme serves as a substrate for the second enzyme and a luminescent energy donor and acceptor pair, e.g., an energy donor or acceptor and a fluorescent compound. The signal will usually be initiated by and/or detected as electromagnetic radiation and will preferably be luminescence such as chemiluminescence, fluorescence, electroluminescence or phosphorescence.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the entactogen analyte present in a sample above the predetermined cut-off level. Temperatures during measurements generally range from about 10° to about 70° C., more usually from about 20° to about 45° C., more usually about 20° to about 25° C. In one approach standard curves are formed using known concentrations of the analytes to be screened. Calibrators and other controls may also be used.

The description below of certain exemplary embodiments of methods uses the language "and/or," which means that the method may or may not involve each item mentioned. This language is used for the sake of brevity. In general, a method will involve at least one antibody for an analyte, e.g., methylenedioxyamphetamine, and at least one enzyme conjugate that corresponds to that analyte, e.g., an enzyme conjugate of a methylenedioxyamphetamine.

One embodiment is a method for determining amphetamine and/or methamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:
(i) said sample,
(ii) an antibody for methylenedioxyamphetamine, and/or
(iii) an antibody for methylenedioxymethamphetamine, and/or
(iv) an antibody for methylenedioxyethamphetamine, and
(iv) a compound of the formula:

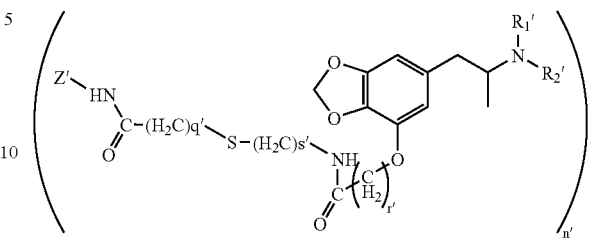

wherein:
$R^{1\prime}$ is H,
$R^{2\prime}$ is H, methyl or ethyl,
r' is 1 to 5,
s' is 1 to 5,
q' is 1 to 5,
Z' is an enzyme,
n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

One embodiment is a method for determining methylenedioxyamphetamine and/or methylenedioxymethamphetamine and/or methylenedioxyethamphetamine in a sample suspected of containing methylenedioxyamphetamine and/or methylenedioxy-methamphetamine and/or methylenedioxyethamphetamine, said method comprising:

(a) providing in combination in a medium:
(i) said sample,
(ii) an antibody for methylenedioxyamphetamine, and/or
(iii) an antibody for methylenedioxymethamphetamine, and/or
(iv) an antibody for methylenedioxyethamphetamine, and
(v) a compound of the formula:

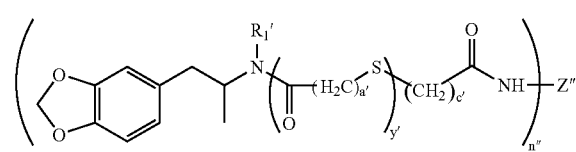

wherein:
R$^{1'}$ is H, or methyl, or ethyl,
a' is 1 to 5,
y' is 1,
Z' an enzyme, for example, G6PDH,
c' is 1 to 5,
n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxymethamphetamine in said sample.

The examining may comprise measuring signal from the enzyme, the amount thereof being related to the presence of the methylenedioxyarnphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

One embodiment is a method for determining methylenedioxyamphetamine and/or methylenedioxymethamphetamine and/or methylenedioxyethamphetamine in a sample suspected of containing methylenedioxyamphetamine and/or methylenedioxymethamphetamine and/or methylenedioxyethamphetamine, said method comprising:
(a) providing in combination in a medium:
(i) said sample,
(ii) a conjugate of an enzyme and a methylenedioxyamphetamine analog and/or a conjugate of an enzyme and a methylenedioxymethamphetamine analog and/or a conjugate of an enzyme and a methylenedioxyethamphetamine analog,
(iii) an antibody for methylenedioxyamphetamine, said antibody being raised against a compound of the formula:

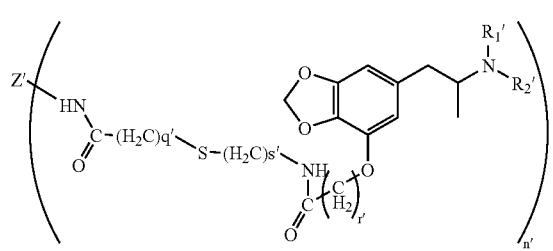

wherein:
R$^{1'}$ is H,
R$^{2'}$ is H,
r' is 1 to 5,
s' is 1 to 5,
q' is 1 to 5,
Z' is an immunogenic protein or a non-poly(amino acid) immunogenic carrier, n" is an integer between 1 and the molecular weight of said immunogenic protein or said immunogenic carrier divided by about 500; and/or
(iv) an antibody for methylenedioxymethamphetamine, said antibody being raised against a compound of the formula:

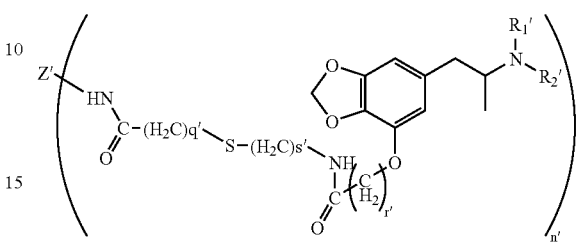

wherein:
R$^{1'}$ is H,
R$^{2'}$ is methyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500; and/or
(v) an antibody for methylenedioxyethamphetamine, said antibody being raised against a compound of the formula:

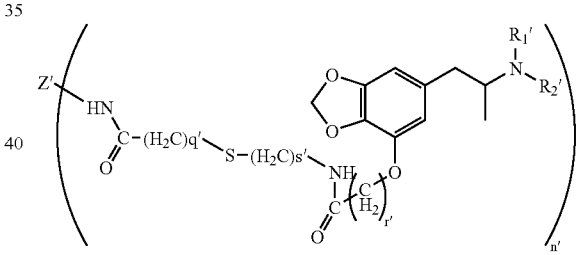

wherein:
R$^{1'}$ is H,
R$^{2'}$ is ethyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

Another embodiment is a method for determining methylenedioxyamphetamine and/or methylenedioxymethamphetamine in a sample suspected of containing methylenedioxyamphetamine and/or methylenedioxymethamphetamine, said method comprising:

(a) providing in combination in a medium:
(i) said sample,
(ii) a conjugate of an enzyme and an methylenedioxyamphetamine analog and/or a conjugate of an enzyme and a methylenedioxymethamphetamine analog and/or a conjugate of an enzyme and a methylenedioxyethamphetamine analog,
(iii) an antibody for methylenedioxyamphetamine, said antibody being raised against a compound of the formula:

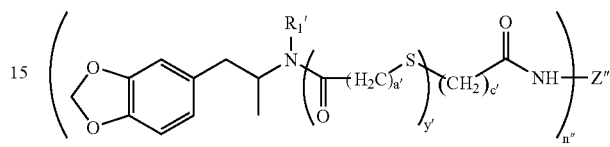

wherein:
$R_{1'}$ is H,
$a'$ is 1 to 5,
$y'$ is 1,
$Z''$ is an immunogenic protein or a non-poly(amino acid) immunogenic carrier,
$c'$ is 1 to 5,
$n''$ is an integer between 1 and the molecular weight of said immunogenic protein or said immunogenic carrier divided by about 500; and/or
(iv) an antibody for methylenedioxymethamphetamine, said antibody being raised against a compound of the formula:

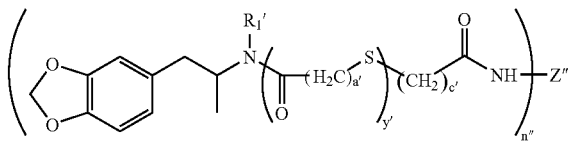

wherein:
$R_{1'}$ is methyl,
$a'$ is 1 to 5,
$y'$ is 1,
$Z''$ is an immunogenic protein or a non-poly(amino acid) immunogenic carrier,
$c'$ is 1 to 5,
$n''$ is an integer between 1 and the molecular weight of said immunogenic protein or said immunogenic carrier divided by about 500; and/or
(v) an antibody for methylenedioxyethamphetamine, said antibody being raised against a compound of the formula:

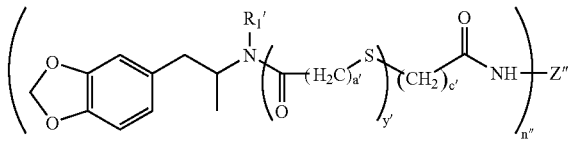

wherein:
$R_{1'}$ is ethyl,
$a'$ is 1 to 5,
$y'$ is 1,
$Z''$ is an immunogenic protein or a non-poly(amino acid) immunogenic carrier,
$c'$ is 1 to 5,
$n''$ is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said amphetamine and/or methamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

Kits

Another aspect relates to kits useful for conveniently performing an assay for the determination of an ecstasy analyte such as, for example, 3,4-methylenedioxyamphetamine (MDA), 3,4-methylenedioxy-methamphetamine (MDMA) and/or 3,4-methylenedioxyethyl-amphetamine (MDEA). The kit comprises (a) an antibody raised against a conjugate of a protein and a compound of Formula I, Formula II or Formula III and (b) ancillary reagents for determining the compound. The kit may further comprise a label conjugate of the compound of Formula I, Formula II or Formula III above.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The description below of certain exemplary embodiments of kits uses the language "and/or," which means that the kit may or may not contain each item mentioned. This language is used for the sake of brevity. In general, a kit will include at least one antibody for an analyte, e.g., methylenedioxyamphetamine, and at least one enzyme conjugate that corresponds to that analyte, e.g., an enzyme conjugate of a methylenedioxyamphetamine.

A particular embodiment is a kit comprising in packaged combination:

(i) an antibody for methylenedioxyamphetamine, and/or
(ii) an antibody for methylenedioxymethamphetamine, and/or
(iii) an antibody for methylenedioxyethamphetamine, and
(iv) a compound of the formula:

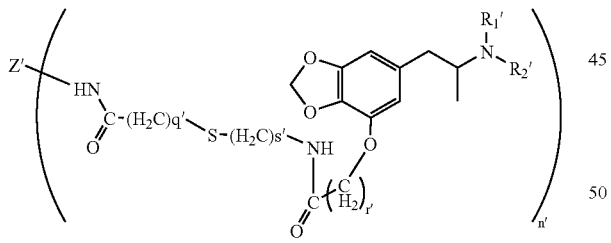

wherein:
$R^{1'}$ is H,
$R^{2'}$ is H, methyl, or ethyl,
r' is 1 to 5,
s' is 1 to 5,
q' is 1 to 5,
Z' is an enzyme such as, for example, glucose-6-phosphate dehydrogenase,
n' is an integer between 1 and the molecular weight of said enzyme divided by about 500.

Another embodiment of a kit comprises in packaged combination:

(i) an antibody for methylenedioxyamphetamine,
(ii) an antibody for methylenedioxymethamphetamine, and/or
(iii) an antibody for methylenedioxyethamphetamine, and
(iv) a compound of the formula:

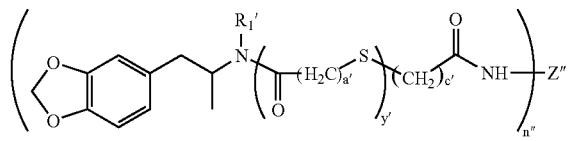

wherein:
$R^{1'}$ is H, methyl or ethyl,
a' is 1 to 5, usually 1,
y' is 0 or 1,
Z' is an enzyme such as, for example, glucose-6-phosphate dehydrogenase,
c' is 1 to 5,
n' is an integer between 1 and the molecular weight of said enzyme divided by about 500.

Another embodiment of a kit comprises in packaged combination:

(i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog, and (ii) an antibody for methylenedioxyamphetamine, said antibody being raised against a compound of the formula:

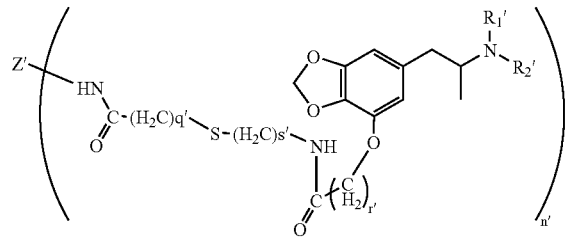

wherein:
$R^{1'}$ is H,
$R^{2'}$ is H,
r' is 1 to 5,
s' is 1 to 5,
q' is 1 to 5,
Z' is an immunogenic protein or a non-poly(amino acid) immunogenic carrier,
n'' is an integer between 1 and the molecular weight of said immunogenic protein or said immunogenic carrier divided by about 500; and/or (iii) an antibody for methylenedioxymethamphetamine, said antibody being raised against a compound of the formula:

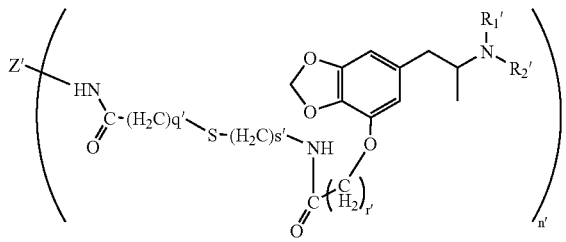

wherein:
$R^{1\prime}$ is H,
$R^{2\prime}$ is methyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500, and/or
(iv) an antibody for methylenedioxyethamphetarnine, said antibody being raised against a compound of the formula:

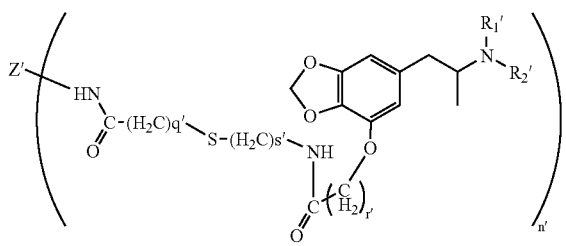

wherein:
$R^{1\prime}$ is H,
$R^{2\prime}$ is ethyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500.

Another embodiment is a kit comprising in packaged combination:
(i) a conjugate of an enzyme and a methylenedioxyamphetamine analog and/or a conjugate of an enzyme and a methylenedioxymethamphetamine analog, and/or a conjugate of an enzyme and a methylenedioxyethamphetarnine analog, and
(ii) an antibody for methylenedioxyamphetamine, said antibody being raised against a compound of the formula:

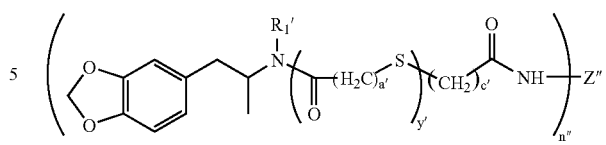

wherein:
$R^{1\prime}$ is H,
a' is 1 to 5,
y' is 0 or 1, usually 1,
Z" is an immunogenic protein or a non-poly(amino acid) immunogenic carrier,
c' is 1 to 5,
n" is an integer between 1 and the molecular weight of said immunogenic protein or said immunogenic carrier divided by about 500; and/or
(iii) an antibody for methylenedioxymethamphetamine, said antibody being raised against a compound of the formula:

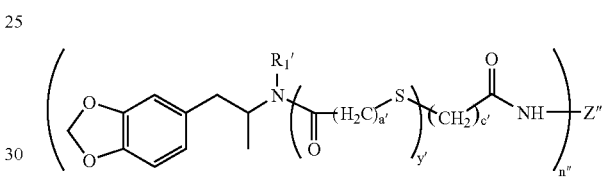

wherein:
$R^{1\prime}$ is methyl,
a' is 1 to 5,
y' is 0 or 1, usually 1,
Z" is an immunogenic protein or a non-poly(amino acid) immunogenic carrier,
c' is 1 to 5,
n" is an integer between 1 and the molecular weight of said immunogenic protein or said immunogenic carrier divided by about 500, and/or
(iv) an antibody for methylenedioxyethamphetamine, said antibody being raised against a compound of the formula:

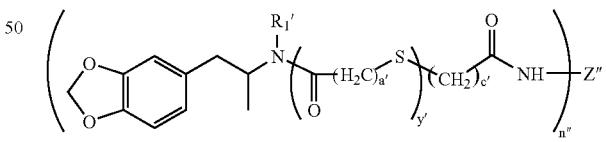

wherein:
$R^{1\prime}$ is ethyl,
a' is 1 to 5,
y' is 0 or 1, usually 1,
Z" is an immunogenic protein or a non-poly(amino acid) immunogenic carrier,
c' is 1 to 5,
n" is an integer between 1 and the molecular weight of said immunogenic protein or said immunogenic carrier divided by about 500.

EXAMPLES

The invention is demonstrated further by the following illustrative examples. Parts and percentages recited herein are by weight unless otherwise specified. Temperatures are in degrees centigrade (° C.). Analytical thin layer chromatography (TLC) was the usual analysis method, performed on Analtech Uniplate Silica Gel GF (0.25 mm) glass-backed plates using the specified solvent. The spots on TLC were visualized by ultraviolet light (short and /or long wave) and/or iodine vapors. Flash chromatography was carried out on Whatman silica gel 60 Å (230–400 mesh). All chemicals were obtained from Sigma, Aldrich, Fluka, and Lancaster and used as received. $^1$H-NMR and $^{13}$C-NMR spectra were routinely recorded on a Bruker Ultrashiel™-400 (400 MHz) spectrometer. Chemical shift were reported in parts per million (ppm, δ) and related to tetramethylsilane or with deuterated solvent as internal reference. NMR abbreviations used are s (singlet), d (doublet), dd (double doublet) and m (multiplet). Mass spectra were obtained at the Mass Spectrometry Laboratory, University of California at Berkeley, Berkeley, Calif.

Melting points were determined on a Hoover capillary apparatus and are uncorrected. Infrared spectra were recorded on a Perkin-Elmer 297IR spectrometer. UV-visible absorption spectra were done on a HP 8452A diode array spectrophotometer. Fluorescence measurements were done on a Spex fluorolog spectrophotometer or a Perkin Elmer 650-40 spectrophotometer.

The following abbreviations have the meanings set forth below:

g—grams
mg—milligrams
mL—milliliters
µL—microliters
mmol—millimoles
DMF—dimethyl formamide
THF—tetrahydrofuran
NMR—nuclear magnetic resonance spectroscopy
MHz—megahertz
EDAC—1-ethyl-3-(3-dimethylaminopropyl)carbodiimide hydrochloride (Sigma Chemical Company)
MeOH—methanol
FAB-MS—fast atom bombardment-mass spectrometry
DI water—deionized water
BCA Protein Concentration Assay—Pierce Chemical Company
TNBS—2,4,6-trinitrobenzene sulfonic acid
KLH—keyhole limpet hemocyanin
NHS—N-hydroxysuccinimic ester
tBoc$_2$O—di-tert-butyldicarbonate
TFA—trifluoroacetic acid
AcCN—Acetonitrile
Boc-AA-14—N-{2-[2-(2-tert-Butoxycarbonylamino-ethoxy)-ethoxy]-ethyl}-succinamic acid (14-atomic length linker)
BSA—Bovine Serum Albumine
Carrier Protein—Protein that attached to a hapten rendering hapten immunogenic
DA-10—ethylene glycol bis(2-aminoethyl) ether (10-atomic length linker)
DCC—N,N,-Dicyclohexylcarbodiimide
DIPEA—N,N'-Diisopropylethylamine
DMF—N,N'-Dimethylformamide
DSC—N,N'-Disuccinimidyl carbonate
DTE—Dithioerythritol; 2,3-Dihydroxybutane-1,4-dithiol
EMIT—Enzyme multiplied immunoassay technique
Hapten—A substance that can react specifically with an antibody but itself is incapable of eliciting an immune response
G6PDH—Glucose-6-phosphatase Dehydrogenase
Immunogen—A substance that is capable of eliciting an immune response
MDA—Methylenedioxyamphetamine
MEMA—Methylenedioxymethamphetamine; Ecstasy
MDEA—Methylenedioxyethylamphetamine
PETINIA—Particle enhanced turbidimetric inhibition immunoassay
TEA or Et$_3$N—Triethyl amine
TFA—Trifluoroacetic acid
TLC—Thin Layer Chromatography Preparation of Antibodies The following method may be employed to prepare polyclonal antibodies: Antiserum containing antibodies is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

The following procedure may be employed to prepare monoclonal antibodies: Monoclonal antibodies were produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of an non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In general, antibodies can be purified by known techniques such as chromatography, e.g., DEAE chromatography, ABx chromatography, and the like, filtration, and so forth.

Preparation of Compound (2)

To a solution of 6-methoxypiperonal (1) (4.5 g, 24.98 mmol) in glacial AcOH (30 ml) was added nitroethane (5.5 ml, 76.18 mmol) and ammonium acetate (3.0 g, 38.92 mmol). The reaction mixture was refluxed under nitrogen for 2 hours (oil bath, 118° C.). The reaction was allowed to cool to room temperature. Most of AcOH was removed by rotary evaporation under reduced pressure and the ice-cooled water (50 ml) was added to the mixture. The aqueous phase was extracted with ethyl acetate (4×80 ml). The combined organic phases were washed with water (50 ml), dried over $Na_2SO_4$, filtered and concentrated. The residue was purified by flash column chromatography using ethyl acetate/hexane (2/3) as an eluent to give the desired product (2) (2.25 g, 38% yield). $^1$H-NMR (CDCl$_3$, 400 MHz) δ: 7.97 (s, 2H), 6.65 (s,1H), 6.63 (s, 1H), 3.92 (s, 3H), 2.45 (s, 3H); 13C-NMR (CDCl$_3$, 100 MHz) δ: 149.7, 146.8, 144.1, 137.5, 134.1, 127.0, 111.7 104.1, 102.6, 57.2, 14.57.

Preparation of Compound (4)

To a solution of LiAlH$_4$ (2 g, 52.7 mmol) in diethyl ether (40 ml) was added slowly a solution of 2 (2.25 g, 9.49 mmol) in diethyl ether (20 ml) and toluene (20 ml). The reaction mixture was refluxed under nitrogen for 4 hours and allowed to cool to room temperature. The excess of LiAlH$_4$ was carefully destroyed at −20° C. by adding water (20 ml) slowly. The residue was filtered and washed with ethyl acetate (3×50 ml). The aqueous phase was separated. The combined organic phase was dried over $Na_2SO_4$, filtered and concentrated to give the crude intermediate compound (3) (1.89 g, 95%) for next reaction.

To a solution of 3 (1.29 g, 6.16 mmol) in $CH_2Cl_2$ (35 ml) was added trifluoroacetic anhydride (5 ml, 35.4 mmol), $K_2CO_3$ (500 mg, 3.62 mmol) and triethylamine (1.8 ml, 12.9 mmol). The reaction was stirred at room temperature for 16 hours. Water (20 ml) was added and the organic phase was separated. The aqueous phase was extracted with $CH_2Cl_2$ (4×30 ml). The combined organic phase was dried over $Na_2SO_4$, filtered and concentrated. The residue was purified by flash column chromatography using ethyl acetate/hexane (3/7) as an eluent to give the desired product (4) (849 mg, 45% yield). $^1$H-NMR (CDCl$_3$, 400 MHz) δ: 6.37 (s, 1H), 6.32 (s, 1H), 5.97 (s, 2H), 4.23 (m, 1H), 3.90 (s, 3H), 2.81 (dd, J=5.9 Hz, 3.8 Hz, 1H), 2.72 (dd, J=7 Hz, 4.0 Hz, 1H), 1.24 (d, J=6.7 Hz, 3H); $^{13}$C-NMR (CDCl$_3$, 100 MHz) δ: 156.7 (q), 149.4, 144.0, 134.6, 131.4, 116 (d), 108.9, 103.8, 101.8, 57.0, 47.7, 42.2, 19.8.

Preparation of Compound (5)

To a solution of 4 (0.849 g, 2.78 mmol) in quinoline (8.0 ml) was added iodotrimethylsilane (0.6 ml, 4.22 mmol). The reaction mixture was heated at 180° C. under nitrogen for 70 minutes (oil bath). The reaction was allowed to cool to room temperature and poured to ice-cooled 10% HCl aqueous solution (15 ml). The aqueous phase was extracted with diethyl ether (4×40 mL). The combined organic solvent was removed by rotary evaporation. The residue was dissolved in MeOH (25 ml) and stirred for 1 hour. MeOH was removed by rotary evaporation. The residue was purified by flash column chromatography using ethyl acetate/hexane (3/7) as an eluent to give the desired product (5) (357 mg, 44% yield). $^1$H-NMR (CDCl$_3$, 400 MHz)δ: 6.58 (dd, J=8.1 Hz, 1H), 6.33 (s, 1H), 6.29 (s, 1H), 5.92 (s, 2H), 4.20 (m, 1H), 2.75 (dd, J=7.0 Hz, 6.3 Hz, 1H), 2.64 (dd, J=7.0 Hz, 7.1 Hz, 1H), 1.21 (d, J=6.7 Hz, 3H); $^{13}$C-NMR (CDCl$_3$, 100 MHz) δ: 157.2 (q), 149.4, 140.0, 133.5, 131.7, 116.2 (d), 112.2, 103.0, 101.7, 48.0, 42.0, 19.7.

Preparation of Compound (6)

To a solution of 5 (357 mg, 1.226 mmol) in THF (15 ml) was added $K_2CO_3$ (800 mg, 5.8 mmol) and tert-butyl bromoacetate (0.8 ml, 5.41 mmol). The reaction mixture was stirred at 50° C. for 16 hours. THF was removed by rotary evaporation. The residue was purified by flash column chromatography using ethyl acetate/hexane (1/4) as an eluent to give the desired product (6) (396 mg, 80% yield). $^1$H-NMR (CDCl$_3$, 400 MHz) δ: 6.57 (dd, J=7.8 Hz, 1H), 6.36 (s, 1H), 6.30 (s, 1H), 5.91 (s, 2H), 4.61 (s, 2H), 4.19 (m, 1H), 2.80 (dd, J=5.9 Hz, 5.8 Hz, 1H), 2.63 (dd, J=7.4 Hz, 7.4 Hz, 1H), 1.47 (s, 9H), 1.18 (d, J=6.7 Hz, 3H); $^{13}$C-NMR (CDCl$_3$, 100 MHz) δ: 168.4, 156.9 (q), 149.8, 141.9, 134.4, 131.7, 116.2(d), 111.6, 104.2, 101.7, 82.8, 67.3, 47.8, 42.0, 28.4, 19.6.

Preparation of Compound (7)

To a solution of 6 (396 mg, 0.977 mmol) in $CH_2Cl_2$ (2 mL) was added TFA (2 mL). The reaction mixture was stirred at room temperature for 0.5 hours. TLC analysis of the mixture showed that starting material 6 disappeared and a new spot displayed at baseline (silica gel, ethyl acetate/hexane=1/4). Most of $CH_2Cl_2$ and TFA were removed by rotary evaporation. The residue was put in high vacuum to remove trace of TFA. This gave the desired product, (7) (336 mg, 98%). $^1$H-NMR (CD$_3$OD, 400 MHz) δ: 6.42 (s, 2H), 5.90 (s, 2H), 4.74 (s, 2H), 4.13 (m, 1H), 2.70 (m, 2H), 1.15 (d, J=6.7 Hz, 3H).

Preparation of Compound (8)

To a solution of 7 (168 mg, 0.481 mmol) in THF (10 ml) was added DCC (200 mg, 0.97 mmol) and NHS ester (120 mg, 1.04 mmol). The reaction mixture was stirred at room temperature for 16 hours. The precipitate from the reaction was filtered off. TLC analysis of the mixture showed that a less polar spot displayed in comparison with 7. To this solution was added diisopropylethylamine (0.5 ml, 2.86 mmol) and methyldithioethylamine hydrochloride (154 mg, 0.964 mmol). The reaction was stirred at room temperature for 2 hours. Most of THF was evaporated by rotary evaporation. The residue was purified by flash column chromatography (silica gel) using ethyl acetate/hexane (1/1) to give the desired product (8) (173 mg, 79% yield). $^1$H-NMR (CDCl$_3$, 400 MHz) δ: 7.06(m, 1H), 6.56 (d, J=7.4 Hz, 1H), 6.43 (s, 1H), 6.35 (s, 1H), 5.96 (s, 2H), 4.58 (s, 2H), 4.20 (m, 1H), 3.69 (q, J=6.12 Hz, 2H), 2.86 (t, J=6.3 Hz, 2H), 2.78 (m, 1H), 2.69 (m, 1H), 2.41 (s, 3H), 1.22 (d, J=6.6 Hz, 3H); $^{13}$C-NMR (CDCl$_3$, 100 MHz) δ: 168.7, 157.0 (q), 150.0, 141.3, 135.0, 132.3, 116.2 (d), 111.5, 105.1, 102.0, 69.5, 47.9, 42.2, 38.2, 37.1, 23.5, 19.6.

Preparation of Compound (9)

To a solution of 8 (117 mg, 0.257 mmol) in MeOH (8.0 ml) and H$_2$O (0.4 ml) was added $K_2CO_3$ (250 mg, 1.81 mmol). The reaction mixture was stirred under nitrogen at room temperature for 16 hours. TLC analysis of the mixture (silica gel, ethyl acetate/hexane=1/1) showed that a more polar spot displayed as a product and starting material (8) still displayed. The reaction was stirred and heated at 50° C. under nitrogen for 6 hours until the starting material (8) was undetectable by TLC analysis. MeOH and water were evaporated by rotary evaporation and the residue was put in high vacuum line for 18 hours to remove a trace of water. The residue was dissolved in 2 ml of MeOH/CH$_2$Cl$_2$ (1/9).

The K₂CO₃ was filtered off. The same procedure was repeated a couple of times until all K₂CO₃ removed. This gave the dimer (9) (0.1285 mmol). (9): ¹H-NMR (CD₃OD, 400 MHz) δ: 6.45 (s, 2H), 5.94 (s, 2H), 4.63 (s, 2H), 3.59 (t, J=6.6 Hz, 2H), 3.04 (m, 1H), 2.88 (t, J=6.6 Hz, 2H), 2.52 (m, 2H), 1.08 (d, J=6.2 Hz, 3H).

Preparation of MDA-KLH Immunogen (12)

a) Preparation of Bromoacetyl KLH (11)

To a solution of KLH (40 mg) in NaH₂PO₄—Na₂HPO₄ buffer (pH=8.0, 0.1M, 10 ml) at 4° C. (ice-bath) was added a solution of bromoacetic acid NHS ester (20 mg, 0.084 mmol) in DMF (0.8 ml). The pH value was maintained at the pH=8.0. The reaction mixture was stirred in the cold-room (4° C.) for 16 hours. The mixture was purified by a Sephadex G-25 column, eluting with NaH₂PO₄—Na₂HPO₄ buffer (pH=8.00, 0.1M). The eluted fractions from the column were monitored by UV at 280 nm. A clean separation between bromoacetyl-KLH and the hapten was obtained. Fractions containing the product were pooled together (32 ml) and concentrated to 8 mL of bromoacetyl-KLH (11) by an AMICON concentrator for the next reaction.

b) Preparation of MDA-KLH Immunogen (12)

To a solution of 9 (80 mg) in degassed (N₂) MeOH (3 mL) was added dithioerythritol (DTE) (20 mg, 0.129 mmol) and Et₃N (0.3 ml). The reaction mixture was stirred at room temperature under nitrogen for 2 hours. MeOH was removed by rotary evaporation and the residue was dried under high vacuum for 2 hours at room temperature to give the desired hapten (10). The activated hapten (10) was dissolved in DMF (0.6 ml) for next reaction.

To a solution of bromoacetyl-KLH (11) (8 ml, pH=8.00) was added the above activated hapten (10) solution slowly at 4° C. under nitrogen. The pH value was maintained at 8.0. The reaction was stirred at 4° C. (cold room) for 16 hours. The reaction mixture was separated using a Sephadex G-25 column, which was equilibrated with NaH₂PO₄—Na₂HPO₄ buffer (pH=7.0, 0.1 M). The UV detector at 280 nm monitored the eluted fractions from the column. A clean separation between KLH immunogen and the hapten was obtained. Fractions containing protein were pooled to a total volume of 41 ml. The concentration of immunogen was measured by using BCA Protein Concentration Assay. The Immunogen (12) had a concentration of 1.05 mg/ml with a hapten number of 1128, and was used for the immunization of sheep, mice and rabbit for antibody production.

Preparation of MDA-BSA Immunogen (14)

a) Preparation of Bromoacetyl BSA (13)

To a solution of BSA (40 mg) in NaH₂PO₄—Na₂HPO₄ buffer (pH=8.0, 0.1M, 6 ml) at 4° C. (ice-bath) was added a solution of bromoacetic acid NHS ester (29 mg, 0.122 mmol) in DMF (0.5 ml). The reaction mixture was stirred in the cold-room (4° C.) for 16 hours. The mixture was purified by a Sephadex G-25 column, eluting with NaH₂PO₄—Na₂HPO₄ buffer (pH=8.00, 0.1M). The eluted fractions from the column were monitored by UV at 280 nm. A clean separation between bromoacetyl-BSA and the hapten was obtained. Fractions containing the product were pooled (33 ml) and concentrated to 8 mL of bromoacetyl-BSA (13) by an AMICON concentrator for the next reaction.

b) Preparation of MDA-BSA Immunogen (14)

To a solution of 9 (0.077 mmol) in degassed (N₂) MeOH (3 mL) was added dithioerythritol (DTE) (11.9 mg, 0.0771 mmol) and Et₃N (0.155 ml). The reaction mixture was stirred at room temperature under nitrogen for 2 hours. MeOH was removed by rotary evaporation and the residue was dried under high vacuum for 2 hours at room temperature to give the desired hapten (10). The activated hapten (10) was dissolved in DMF (0.6 ml) for the next reaction.

To a solution of bromoacetyl-BSA (13) (8 ml, pH=8.00) was added the above activated hapten (10) solution slowly at 4° C. under nitrogen. The pH value was maintained at the pH=8.0. The reaction was stirred at 4° C. (cold room) for 16 hours. The reaction mixture was purified on the Sephadex G-25 column, which was equilibrated with NaH₂PO₄—Na₂HPO₄ buffer (pH=7.0, 0.1 M, 200 mL). The column was eluted with NaH₂PO₄—Na₂HPO₄ buffer (pH=7.0, 0.1 M). The UV detector at 280 nm monitored the eluted fractions from the column. A clean separation between bromoacetyl-BSA and the hapten was obtained. Fractions containing protein were pooled to a total volume of 36.4 ml. The concentration of immunogen was measured by using BCA Protein Concentration Assay. The Immunogen (14) had a concentration of 1.02 mg/ml with the hapten number of 36, and was used for the immunization of sheep, mice and rabbit for antibody production.

Preparation of Compound (16)

To a stirred solution of 4 (1.6669 g, 5.46 mmol) in THF (20 ml) under nitrogen was added KH (730 mg, 18.20 mmol, freed from protective mineral oil by washing with hexane three time). The reaction mixture was stirred for 10 minutes and 18-crown-6 (470 mg) and MeI (4.15 mL, 66.5 mmol) was added to the mixture. The reaction mixture was allowed to stir at room temperature for 1.5 hour and refluxed at 78° C. under nitrogen for 16 hours. Most of THF was removed by rotary evaporation and dichloromethane (30 ml) was added to the mixture followed by cautiously adding of 5% aqueous HCl (30 ml). The organic phase was separated and the aqueous phase was extracted with dichloromethane (3×30 ml) and the combined organic phase was washed with water (2×30 ml) and dried over Na₂SO₄. The organic solvent was filtered and evaporated to dryness by rotary evaporation. The residue was purified by flash column chromatography (silica gel) using ethyl acetate/hexane (1/4) as an eluent to give 16 (1.5814 g, 90% yield). ¹H-NMR (CDCl₃, 400 MHz) δ: 6.31 (m, 2H), 5.91 (s, 2H), 4.72, 4.17 (m, 1H), 3.87 (s, 3H), 2.95 (s, 3H), 2.78–2.65 (m, 2H), 1.20 (d, J=6.9 Hz, 3H).

Preparation of Compound (17)

To a solution of 16 (1.19 g, 3.73 mmol) in quinoline (7.2 ml) was added iodotrimethylsilane (1.1 ml, 7.46 mmol). The reaction mixture was heated at 180° C under nitrogen for 90 minutes (oil bath). The reaction was allowed to cool to room temperature and poured to ice-cooled 50% HCl aqueous solution (25 ml) and diethyl ether (50 ml). The aqueous phase was extracted with diethyl ether (3×50 mL). The combined organic solvent was removed by rotary evaporation. The residue was dissolved in MeOH (25 ml) and stirred for 1 hour. MeOH was removed by rotary evaporation. The residue was purified by flash column chromatography using ethyl acetate/hexane (3/7) as an eluent to give the desired product (17) (527 mg, 46% yield). ¹H-NMR (CDCl₃, 400 MHz) δ: 6.34 (m, 2H), 5.94 (ms, 2H), 4.75, 4.15 (m, 1H), 2.94 (s, 3H), 2.74–2.63 (m, 2H), 1.21 (d, J=6.9 Hz, 3H).

Preparation of Compound (18)

To a solution of 17 (658 mg, 2.16 mmol) in THF (20 ml) was added K₂CO₃ (3.2 g, 21.6 mmol) and tert-butyl bromoacetate (2.6 ml, 17.28 mmol). The reaction mixture was stirred at 50° C. for 16 hours. THF was removed by rotary evaporation. The residue was purified by flash column chromatography using ethyl acetate/hexane (1/3) as an eluent to give the desired product (18) (774 mg, 85% yield). $^1$H-NMR (CDCl$_3$, 400 MHz) δ: 6.41–6.31 (m, 2H), 5.95 (ms, 2H), 4.77, 4.20 (m, 1H), 4.64 (m, 2H), 2.94 (bs, 3H), 2.82–2.63 (m, 2H), 1.50 (s, 9H), 1.21 (d, J=6.90 Hz, 3H).

Preparation of Compound (19)

To a solution of 18 (509 mg, 1.22 mmol) in CH$_2$Cl$_2$ (2 mL) was added TFA (2 mL). The reaction mixture was stirred at room temperature for 0.5 hours. TLC analysis of the mixture showed that the starting material, 18 had disappeared and a new spot was displayed at baseline (silica gel, ethyl acetate/hexane=1/3). Most of CH$_2$Cl$_2$ and TFA were removed by rotary evaporation. The residue was put in high vacuum to remove trace of TFA. This gave the desired product, (19) (518 mg, 100% yield). $^1$H-NMR (CD$_3$OD, 400 MHz) δ: 6.50–6.34 (m, 2H), 5.96 (s, 2H), 4.80 (s, 2H), 4.8, 4.10 (m, 1H), 3.05 (bs, 3H), 2.73–2.70 (m, 2H), 1.22 (d, J=6.8 Hz, 3H).

Preparation of Compound (20)

To a solution of 19 (268 mg, 0.738 mmol) in THF (10 ml) was added DCC (308 mg, 1.49 mmol) and NHS ester (175 mg, 1.52 mmol). The reaction mixture was stirred at room temperature for 16 hours. The precipitate from the reaction was filtered off. TLC analysis of the mixture showed that a less polar spot in comparison with 19. To this solution was added a solution of diisopropylethylamine (0.772 ml, 4.43 mmol) and methyldithioethylamine hydrochloride (236 mg, 1.478 mmol) in THF (2 ml) and DMF (0.8 ml). The reaction was stirred at room temperature for 2 hours. Most of THF and DMF was evaporated by rotary evaporation. The residue was purified by flash column chromatography (silica gel) using ethyl acetate/hexane (1/1) to give the desired product (20) (221 mg, 64% yield). $^1$H-NMR (CDCl$_3$, 400 MHz) δ: 6.46–6.29 (m, 2H), 5.98 (s, 2H), 4.80, 4.10 (m, 1H), 4.61 (s, 2H), 3.70 (t, J=6.3 Hz, 2H), 3.10 (s, 3H), 2.86 (t, J=6.4 Hz, 2H), 2.60–2.80 (m, 2H), 2.42 (s, 3H), 1.21 (d, J=6.8 Hz, 3H).

Preparation of Compound (21)

To a solution of 20 (120 mg, 0.257 mmol) in MeOH (8.0 ml) and H$_2$O (0.4 ml) was added K$_2$CO$_3$ (241 mg, 1.738 mmol). The reaction mixture was stirred under nitrogen at room temperature for 18 hours. TLC analysis of the mixture (silica gel, ethyl acetate/hexane=1/1) showed a more polar product spot in comparison with starting material (20). MeOH and water were evaporated by rotary evaporation and the residue was put in high vacuum line to remove a trace of water. The residue was dissolved in 2 ml of MeOH/CH$_2$Cl$_2$ (1/9). The K$_2$CO$_3$ was filtered off. The same procedure was repeated a couple of times until all K$_2$CO$_3$ removed This gave a theoretical yield of dimer 21 (0.1285 mmol): $^1$H-NMR (CD$_3$OD, 400 MHz) δ: 6.58–6.43 (m, 2H), 5.93 (s, 2H), 4.61 (s, 2H), 3.60 (t, J=6.7 Hz, 2H), 2.86 (t, J 6.6 Hz, 2H), 2.71–2.68 (m, 2H), 2.44 (m, 1H), 2.36 (s, 3H), 1.00 (d, J=6.12 Hz, 3H).

Preparation of MDMA-KLH Immunogen (23)

a) Preparation of Bromoacetyl KLH (11)

To a solution of KLH (40 mg) in NaH$_2$PO$_4$—Na$_2$HPO$_4$ buffer (pH=8.0, 0.1M, 8 ml) at 4° C. (ice-bath) was added a solution of bromoacetic acid NHS ester (14.8 mg, 0.0624 mmol) in DMF (0.5 ml). The pH was maintained at 8.0. The reaction mixture was stirred in the cold-room (4° C.) for 16 hours. The mixture was purified by a Sephadex G-25 column, eluting with NaH$_2$PO$_4$—Na$_2$HPO$_4$ buffer (pH=8.00, 0.1M). The eluted fractions from the column were monitored by UV at 280 nm. A clean separation between bromoacetyl-KLH and the hapten was obtained. Fractions containing the product were pooled and concentrated to 9 ml of bromoacetyl-KLH (11) by an AMICON concentrator for the next reaction.

b) Preparation of MDMA-KLH Immunogen (23)

To a solution of 21 (0.1285 mmol) in degassed (N$_2$) MeOH (5 mL) was added dithioerythritol (DTE) (20.6 mg, 0.1285 mmol) and Et$_3$N (0.3 ml). The reaction mixture was stirred at room temperature under nitrogen for 2 hour. MeOH was removed by rotary evaporation and the residue was dried under high vacuum for 2 hours at room temperature to give the desired thiol (22). The activated hapten (22) was dissolved in DMF (0.5 ml) for the next reaction.

To a solution of bromoacetyl-KLH (11) (9 ml, pH=8.00) was added the above activated hapten (22) solution slowly at 4° C. under nitrogen. The pH was maintained at 8.0. The reaction was stirred at 4° C. (cold room) for 16 hours. The reaction mixture was separated on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein were pooled to a total volume of 34 ml. The concentration of immunogen was measured by using BCA Protein Concentration Assay. The Immunogen (23) had a concentration of 2.17 mg/ml with a hapten number of 1728 and was used for the immunization of sheep, mice and rabbit for antibody production.

Preparation of bromoacetyl BSA (24)

a) Preparation of Bromoacetyl BSA (11)

To a solution of BSA (120 mg) in NaH$_2$PO$_4$—Na$_2$HPO$_4$ buffer (pH=8.0, 0.1M, 10 ml) at 4° C. (ice-bath) was added a solution of bromoacetic acid NHS ester (85.2 mg, 0.359 mmol) in DMF (0.5 ml). The pH value was maintained at 8.0. The reaction mixture was stirred in the cold-room (4° C.) for 16 hours. The mixture was purified by a Sephadex G-25 column, eluting with NaH$_2$PO$_4$—Na$_2$HPO$_4$ buffer (pH=8.00, 0.1M). The eluted fractions from the column were monitored by UV at 280 nm. A clean separation between bromoacetyl-BSA and the hapten was obtained. Fractions containing the product were pooled and concentrated to 10 mL of bromoacetyl-BSA (13) by an AMICON concentrator for next reaction.

b) Preparation of MDMA-BSA Immunogen (24)

To a solution of 21 (0.4697 mmol) in degassed (N$_2$) MeOH (10 mL) was added dithioerythritol (DTE) (72.6 mg, 0.47 mmol) and Et$_3$N (1.11 ml). The reaction mixture was stirred at room temperature under nitrogen for 3 hours. MeOH was removed by rotary evaporation and the residue was dried under high vacuum for 1 hour at room temperature to give the desired thiol (22). The activated hapten (22) was dissolved in DMF (1 ml) for next reaction.

To a solution of bromoacetyl-BSA (11) (10 ml, pH=8.00) was added the above activated hapten (22) solution slowly at 4° C. under nitrogen. The pH was maintained at 8.0. The reaction was stirred at 4° C. (cold room) for 16 hours. The reaction mixture was separated on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between BSA immunogen and the hapten was obtained. Fractions containing protein were pooled to a total volume of 42.5 ml. The concentration of immunogen was measured by using BCA Protein Concentration Assay. The Immunogen (24) had a concentration of 2.64 mg/ml with a hapten number of 28.

Preparation of Compound (25)

To a solution of 19 (92.3 mg, 0.254 mmol) in MeOH (8.0 ml) and H$_2$O (0.4 ml) was added K$_2$CO$_3$ (350 mg, 2.54 mmol). The reaction mixture was stirred at room temperature for 18 hours. TLC analysis of the mixture (silica gel, ethyl acetate/hexane=1/1) showed that a more polar spot displayed as a product in comparison with staring material (19). MeOH was evaporated by rotary evaporation and the residue was dissolved in THF (3 ml) and water (0.5 mL). To this solution was added K$_2$CO$_3$ (290 mg, 2.10 mmol) and t-Boc$_2$O (182.1 mg, 0.834 mmol). The reaction mixture was stirred at room temperature for 2 hours. THF was removed by rotary evaporation and water (4.5 ml) was added. The aqueous was acidified with acetic acid to pH=4.0. The aqueous was extracted with CH$_2$Cl$_2$ (4×10 ml). The combined organic phase was washed with water (10 ml), dried over MgSO$_4$, filtered and concentrated. The residue was purified by flash column chromatography using MeOH/CH$_2$Cl$_2$ (12/88) as an eluent to give the desired product (25) (50 mg, 54% yield in two steps) (25): $^1$H-NMR (CD$_3$OD, 400 MHz) δ: 6.44–6.39 (m, 2H), 5.91 (bs, 2H), 4.74 (bs, 2H), 4.28 (m, 1H) 2.79 (bs, 3H), 2.69–2.54 (m, 2H), 1.48–1.39 (m, 9H), 1.29–1.16 (m, 3H).

Preparation of Compound (26)

To a solution of 25 (50 mg, 0.136 mmol) in THF (3 ml) was added DCC (70 mg, 0.339 mmol) and NHS (30 mg, 0.261 mmol). The reaction mixture was stirred at room temperature for 16 hours. The precipitate from the reaction was filtered off. TLC analysis of the mixture showed that a less polar spot displayed in comparison with 25. To this solution was added a solution of diisopropylethylamine (0.2 ml, 1.15 mmol) and 2-maleimidoethylamine trifluoroacetic acid (88 mg, 0.346 mmol) in THF (1 ml). The reaction was stirred at room temperature for 1 hour. Most of THF was evaporated by rotary evaporation. The residue was purified by flash column chromatography (silica gel) using ethyl acetate/hexane (7/3) to give the desired product (26) (34 mg, 51% yield). $^1$H-NMR (CDCl$_3$, 400 MHz) δ: 6.93 (m, 1H, NH), 6.71 (s, 2H), 6.40 (m, 2H), 5.95 (s, 2H), 4.55 (s, 2H), 4.30 (m, 1H), 3.75 (m, 2H), 3.56 (t, J =5.9 Hz, 2H), 2.81 (s, 3H), 2.78–2.52 (m, 2H), 1.49–1.36 (m, 9H), 1.26–1.10 (m, 3H).

Preparation of Compound (27)

To a solution of 26 (7 mg, 0.0143 mmol) in CH$_2$Cl$_2$ (1 mL) was added TFA (0.2 mL). The reaction mixture was stirred at room temperature for 2 hours. TLC analysis of the reaction showed that starting material (26) disappeared and a new more polar spot displayed (silica gel, ethyl acetate/hexane=7/3). Most of CH$_2$Cl$_2$ and TFA were removed by rotary evaporation under reduced pressure. The residue was further dried under high vacuum to remove trace of TFA. This gave the desired product (27) (7 mg, 97% yield). ). $^1$H-NMR (CDCl$_3$, 400 MHz) δ: 6.72 (s, 2H), 6.65–6.42 (m, 2H), 5.97 (s, 2H), 4.60 (s, 2H), 3.73 (m, 2H), 3.56 (m, 2H), 3.40 (m, 1H), 2.77–2.70 (m, 3H), 1.95 (m, 2H), 1.75 (m, 2H), 1.26–1.22 (m 3H).

Preparation of Compound (28)

To a solution of MDMA (58 mg, 0.2525 mmol) in DMF (8 ml) was added NaH (40 mg). The reaction mixture was stirred at room temperature for 20 minutes. Methyl bromoacetate (50 mg) was added to the mixture. The mixture was stirred at room temperature for 4 hours. DMF was removed by rotary evaporation and water (5 mL) was added. The aqueous phase was extracted with ethyl acetate (4×30 ml). The combined organic phases were dried over MgSO$_4$, filtered and concentrated. The residue was purified by flash column chromatography using ethyl acetate/hexane (2/3) as an eluent to give the desired product (28) (63 mg, 94% yield); $^1$H-NMR (CDCl$_3$, 400 MHz) δ: 6.74 (d, J=7.8 Hz, 1H), 6.69 (s, 1H), 6.62 (d, J=7.9 Hz, 1H), 5.94 (s, 2H), 3.76 (s, 3H), 3.33 (s, 2H), 2.92 (m, 2H), 2.43 (s, 3H), 2.33 (m, 1H), 0.95 (d, J=6.5 Hz, 3H).

Preparation of Compound (29)

To a solution of 28 (63 mg, 0.2375 mmol) in MeOH (5 mL) and H$_2$O (0.5 mL) was added NaOH (200 mg). The reaction mixture was stirred at room temperature for 2 hours. HCl (6N) was added to maintain the pH at 2.0. Most of MeOH and H$_2$O were removed by rotary evaporation. The residue was purified by flash column chromatography using CH$_2$Cl$_2$/MeOH (9/1) as an eluent to give the desired product (29) (32 mg, 47% yield); $^1$H-NMR (CD$_3$OD, 400 MHz) δ: 6.81 (m, 3H), 5.95 (s, 2H), 4.09 (m, 2H), 3.66 (m, 1H), 3.23 (m, 1H), 2.94 (s, 3H), 2.76 (m, 1H), 1.22 (d, J=6.6 Hz, 3H).

Preparation of MDMA-BSA Immunogen (31)

To a solution of 29 (32 mg, 0.1112 mmol) in DMF (0.8 mL) was added EDAC (70 mg, 0.365 mmol) and NHS (63 mg, 0.547 mmol). The reaction was stirred at room temperature under argon for 16 hours. The activated hapten (30) was added dropwise under argon to 8 mL of sodium phosphate solution (0.1M, pH=8.0) of BSA (60 mg) at 4° C. under argon. The pH value changed during the addition and 0.1 N of NaOH aqueous solution was used to maintain the pH at 8.0. After completed the addition, the solution was allowed to stir at room temperature for 16 hours. The reaction mixture was separated on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein were pooled to a total volume of 30.5 ml. The concentration of protein was measured by using BCA Protein Concentration Assay. The immunogen (31) had a concentration of 1.74 mg/ml and was used for the immunization of mice, rabbit and sheep for antibody production.

Preparation of Compound (32)

To a solution of MDEA (50 mg, 0.205 mmol) in DMF (8 mL) was added NaH (50 mg). The reaction mixture was stirred at room temperature for 20 minutes. Methyl bromoacetate (64.6 mg) was added to the mixture. The mixture was stirred at room temperature for 4 hours. DMF was removed by rotary evaporation and water (6 mL) was added. The aqueous phase was extracted with ethyl acetate (4×25 mL). The combined organic phases were dried over MgSO$_4$, filtered and concentrated. The residue was purified by flash column chromatography using ethyl acetate/hexane (2/3) as an eluent to give the desired product (32) (30.2 mg, 53% yield); $^1$H-NMR (CDCl$_3$, 400 MHz δ: 6.72 (d, J=7.8 Hz, 1H), 6.69 (s, 1H), 6.61 (d, J=7.9 Hz, 1H), 5.93 (s, 2H), 3.73 (s, 3H), 3.32 (s, 2H), 3.01(m, 1H), 2.91–2.87 (m, 1H), 2.68 (m, 2H), 2.30 (m, 1H), 1.09 (t, J=7.1 Hz, 3H), 0.91 (d, J=6.3 Hz, 3H). $^{13}$C-NMR (CDCl$_3$, 100 MHz) δ: 173.6, 147.8, 144.8, 134.5, 122.7, 109.9, 108.4, 101.2, 59.2, 52.1, 51.8, 46.2, 40.2, 15.3, 14.2.

Preparation of Compound (33)

To a solution of 32 (30.2 mg, 0.108 mmol) in MeOH (6 mL) and H$_2$O (0.6 mL) was added NaOH (90 mg). The reaction mixture was stirred at room temperature for 2 hours. HCl (6N) was added to maintain the pH at 2.0. Most of MeOH and H$_2$O were removed by rotary evaporation. The residue was purified by flash column chromatography using CH$_2$Cl$_2$/MeOH (85/15) as an eluent to give the desired product (33) (20.3 mg, 62% yield); $^1$H-NMR (CD$_3$OD, 400 MHz) δ: 6.79 (m, 3H), 5.95 (s, 2H), 4.10 (m, 1H), 3.74 (m, 1H), 3.36 (m, 3H), 3.13 (m, 1H), 2.75 (m, 1H), 1.37 (m, 3H), 1.22 (d, J=6.6 Hz, 3H).

Preparation of MDEA-BSA Immunogen (35)

To a solution of 33 (20.3 mg, 0.0672 mmol) in DMF (0.7 mL) was added EDAC (32.2 mg, 0.168 mmol) and NHS (28 mg, 0.243 mmol). The reaction was stirred at room temperature under argon for 16 hours. The activated hapten (34) was added dropwise under argon to 8 mL of sodium phosphate solution (0.1M, pH=8.0) of BSA (55 mg) at 4° C. under argon. The pH value changed during the addition and 0.1 N of NaOH aqueous solution was used to maintain the pH at 8.0. After the addition, the solution was allowed to stir at room temperature for 16 hours. The reaction mixture was separated on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein were pooled to a total volume of 25.3 ml. The concentration of protein was measured by using BCA Protein Concentration Assay. The immunogen (35) had a concentration of 2.11 mg/ml and used for the immunization of mice for antibody production.

Preparation of Compound (40)

To a stirred solution of MDA (100 mg, 0.4636 mmol) in THF (15 mL) was added diisopropylethylamine (0.5 ml, 2.87 mmol). The reaction was stirred at room temperature for 30 minutes. 2-Mercapto[S-acetyl]acetic acid N-hydroxysuccinimide ester (116 mg, 0.5016 mmol) was added to the reaction mixture under nitrogen. The reaction mixture was stirred at room temperature for 2 hours. TLC analysis of the mixture showed that a less polar spot as a product in comparison with MDA. The organic solvent was removed to dryness by rotary evaporation. The residue was purified by flash column chromatography (silica gel) using ethyl acetate/hexane (1/1) as an eluent to give the desired product (40) (132 mg, 96% yield). $^1$H-NMR (CDCl$_3$, 400 MHz) δ: 6.72 (d, J=7.8 Hz, 1H), 6.64 (s, 2H), 6.60 (s, J=7.8 Hz, 1H), 6.10 (m, 1H), 5.93 (s, 2H), 4.15 (m, 1H), 3.52 (d, j=14.6 Hz, 1H), 3.42 (d, J=14.6 Hz, 1H), 2.66 (m, 2H), 2.39 (s, 3H), 1.10 (d, J=6.7 Hz, 3H). 13C-NMR (CDCl$_3$, 100 MHz) δ: 196.4, 167.8, 147.9, 146.5, 131.8, 122.8, 110.2, 108.5, 101.3, 47.00, 42.3, 33.5, 30.6, 20.2.

Preparation of MDMA-KLH Immunogen (42)

a) Preparation of Bromoacetyl KLH (11)

To a solution of KLH (20 mg) in NaH$_2$PO$_4$—Na$_2$HPO$_4$ buffer (pH=8.0, 0.1M, 3 ml) at 4° C. (ice-bath) was added a solution of bromoacetic acid NHS ester (10 mg, 0.042 mmol) in DMF (0.2 ml). The reaction mixture was stirred in the cold-room (4° C.) for 16 hours. The mixture was purified by a Sephadex G-25 column, eluting with NaH$_2$PO$_4$—Na$_2$HPO$_4$ buffer (pH=8.00, 0.1M). The eluted fractions from the column were monitored by UV at 280 nm. A clean separation between bromoacetyl-KLH and the hapten was obtained. Fractions containing the product were pooled (25 ml) and concentrated to 8 ml by an AMICON concentrator for the next reaction.

b) Preparation of MDA-SH-KLH Immunogen (42)

To a solution of 40 (30.1 mg) in degassed (N$_2$) MeOH (2 ml) and water (0.1 ml) was added K$_2$CO$_3$ (40 mg, 0.29 mmol) under nitrogen. The reaction mixture was stirred at room temperature under nitrogen for 45 minutes. MeOH was filtered and removed by rotary evaporation to give the hapten (41). The activated hapten (41) was dissolved in DMF (0.5 ml) for next reaction.

To a solution of bromoacetyl-KLH (11) (8 ml, pH=8.00) was added the above activated hapten (41) solution slowly at 4° C. under nitrogen. The pH was maintained at 8.0. The reaction was stirred at 4° C. (cold room) for 16 hours. The reaction mixture was separated on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between KLH immunogen and the hapten was obtained. Fractions containing protein were pooled to have a total volume of 34.1 ml. The concentration of immunogen was measured by using BCA Protein Concentration Assay. The Immunogen (42) had a concentration of 0.64 mg/ml with a hapten number of 1448 and was used for the immunization of sheep, mice and rabbit for antibody production.

Preparation of MDA-SH-BSA Immunogen (43)

(a) Preparation of Bromoacetyl BSA (13)

To a solution of BSA (120 mg) in NaH$_2$PO$_4$—Na$_2$HPO$_4$ buffer (pH=8.0, 0.1M, 10 ml) at 4° C. (ice-bath) was added a solution of bromoacetic acid NHS ester (85 mg, 0.3586 mmol) in DMF (0.8 ml). The reaction mixture was stirred in the cold-room (4° C.) for 16 hours. The mixture was purified by a Sephadex G-25 column, eluting with NaH$_2$PO$_4$—Na$_2$HPO$_4$ buffer (pH=8.00, 0.1M). The eluted fractions from the column were monitored by UV at 280 nm. A clean separation between bromoacetyl-BSA and the hapten was obtained. Fractions containing the product were pooled together (46 ml) and concentrated to 12 mL of bromoacetyl-BSA (13) by an AMICON concentrator for the next reaction.

b) Preparation of BSA-Immunogen (43)

To a solution of 40 (82 mg) in degassed (N$_2$) MeOH (3 ml) and water (0.2 ml) was added K$_2$CO$_3$ (100 mg, 0.7246 mmol) under nitrogen. The reaction mixture was stirred at room temperature under nitrogen for 45 minutes. MeOH was filtered and removed by rotary evaporation to give the hapten (41). The activated hapten (41) was dissolved in DMF (0.5 ml) for next reaction.

To a solution of bromoacetyl-BSA (13) (12 ml, pH=8.00) was added the above activated hapten (41) solution slowly at 4° C. under nitrogen. The pH was maintained at 8.0. The reaction was stirred at 4° C. (cold room) for 16 hours. The reaction mixture was purified on the Sephadex G-25 column, which was equilibrated with NaH$_2$PO$_4$—Na$_2$HPO$_4$ buffer (pH=7.0, 0.1 M). The UV detector at 280 nm monitored the eluted fractions from the column. A clean separation between bromoacetyl-BSA and the hapten was obtained. Fractions containing protein were pooled to a total volume of 45.5 ml. The concentration of immunogen was measured by using BCA Protein Concentration Assay. The Immunogen (43) had a concentration of 2.45 mg/ml with a hapten number of 38, and was used for the immunization of sheep, mice and rabbit for antibody production.

Preparation of MDA-AA-14-Boc (47)

To a solution of MDA (100 mg, 0.4636 mmol) in MeOH (5 mL) was added Et$_3$N (0.6 ml). The reaction mixture was stirred at room temperature for 15 minutes. The MeOH was removed by rotary evaporation and the residue was put in high vacuum line for 30 minutes. The residue was dissolved in anhydrous AcCN (1 ml) and denoted as the solution A for the next reaction.

To a solution of DSC (251 mg, 0.98 mmol) and Boc-AA-14 (250 mg, 0.718 mmol) in anhydrous AcCN (5 mL) was added Et$_3$N (0.28 ml). The reaction mixture was stirred at room temperature for 2.5 hours and then Et$_3$N (0.2 ml) and solution A were added to the reaction. The reaction was stirred at room temperature for 16 hours. Most of the solvent was removed by rotary evaporation. The residue was purified by flash column chromatography using CH$_2$Cl$_2$/MeOH (9/1) as an eluent to give the desired product (47) (230 mg, 97% yield). $^1$H-NMR (CDCl$_3$, 400 MHz) δ: 6.72 (b, NH, 1H), 6.67 (d, J=7.8 Hz, 1H), 6.64 (s, 1H), 6.57 (d, J=7.9 Hz, 1H), 6.42 (b, NH, 1H), 5.88 (s, 2H), 5.27 (b, NH, 1H), 4.09 (m, 1H), 3.56–3.50 (m, 8H), 3.40 (m, 2H), 3.28 (m, 2H), 2.69 (m, 1H), 2.53 (m, 1H), 2.50 (m, 4H), 1.40 (s, 9H), 1.05 (d, J=6.6 Hz, 3H). $^{13}$CNMR (CDCl$_3$, 100 MHz) δ: 172.8, 171.8, 156.5, 147.9, 146.4, 132.4, 122.6, 110.1, 108.4, 101.2, 79.6, 70.6, 70.1, 50.8, 46.8, 42.6, 40.7, 39.7, 32.3, 32.1, 28.8, 20.2.

Preparation of MDA-AA-14-NH$_2$ (48)

To a solution of 47 (230 mg, 0.4516 mmol) in CH$_2$Cl$_2$ (2 ml) was added TFA (0.5 ml). The reaction mixture was stirred at room temperature for 1.5 hours. TLC analysis of the reaction showed that the starting material (47) disappeared and a new more polar spot was displayed (silica gel, MeOH/CH$_2$Cl$_2$=1/9). Most of CH$_2$Cl$_2$ and TFA were removed by rotary evaporation under reduced pressure. The residue was further dried under high vacuum for 18 hours to remove trace of TFA. The residue was dissolved in MeOH (5 ml) and NH$_4$OH was added to adjust the pH value to 10. The MeOH and the excess of NH$_4$OH were evaporated under reduced pressure. The residue was purified by flash column chromatography using CH$_2$Cl$_2$MeOH (8/2) as an eluent to give the desired product (48) (126 mg, 68% yield). $^1$H-NMR (CD$_3$OD, 400 MHz) δ: 6.61 (m, 2H), 6.54 (m, 1H), 5.78 (s, 2H), 3.96 (m, 1H), 3.62–3.53 (m, 6H), 3.45 (m, 2H), 3.28 (m, 2H), 3.01 (m, 2H), 2.58 (m, 1H), 2.49 (m, 1H), 2.37 (m, 4H), 0.99 (d, J=6.6 Hz, 3H).

Preparation of MDMA-AA-14-Boc (50)

To a solution of MDMA (50 mg, 0.2176 mmol) in MeOH (5 mL) was added Et$_3$N (0.3 ml). The reaction mixture was stirred at room temperature for 15 minutes. The MeOH was removed by rotary evaporation and the residue was put in high vacuum line for 30 minutes. The residue was dissolved in anhydrous AcCN (1 ml) and denoted as solution A for the next reaction.

To a solution of DSC (78 mg, 0.3046 mmol) and Boc-AA-14 (78 mg, 0.2176 mmol) in anhydrous AcCN (2 mL) was added Et$_3$N (0.076 ml). The reaction mixture was stirred at room temperature for 2.5 hours and then Et$_3$N (0.076 ml) and solution A were added to the reaction. The reaction was stirred at room temperature for 16 hours. Most of the solvent was removed by rotary evaporation. The residue was purified by flash column chromatography using CH$_2$Cl$_2$/MeOH (9/1) as an eluent to give the desired product (50) (49 mg, 43% yield). $^1$H-NMR (CDCl$_3$, 400 MHz) δ: 7.02 (b, NH, 1H), 6.73–6.56 (m, 3H), 5.93–5.92 (bs, 2H), 5.27 (b, NH, 1H), 4.80, 4.15 (m, 1H), 3.61–3.54 (m, 8H), 3.42–3.32 (m, 5H), 2.84, 2.81 (s, 3H), 2.60–2.45 (m, 5H), 1.43 (s, 9H), 1.23 (d, J=6.3 Hz), 1.01 (d, J=6.5 Hz, 3H).

Preparation of MDMA-AA-14-NH$_2$ (51)

To a solution of 50 (49 mg, 0.0936 mmol) in CH$_2$Cl$_2$ (2 ml) was added TFA (0.4 ml). The reaction mixture was stirred at room temperature for 1.5 hours. TLC analysis of the reaction showed that the starting material (50) disappeared and a new more polar spot was displayed (silica gel, MeOH/CH$_2$Cl$_2$=1/9). Most of the CH$_2$Cl$_2$ and TFA were removed by rotary evaporation under reduced pressure. The residue was further dried under high vacuum for 18 hours to remove trace of TFA. This gave the desired product (51) (46 mg, 91.4% yield). $^1$H-NMR (CDCl$_3$, 400 MHz) δ: 6.74–6.69 (m, 1H), 6.61–6.55 (m, 2H), 5.93–5.91 (bs, 2H), 4.80, 4.15 (m, 1H), 3.61–3.54 (m, 8H), 3.42–3.32 (m, 5H), 2.84, 2.81 (s, 3H), 2.60–2.45 (m, 5H), 1.24 (d, J=6.6 Hz, 1.5H), 1.09 (d, J=6.8 Hz, 1.5H).

Preparation of MDEA-AA-14-Boc (53)

To a solution of MDEA (100 mg, 0.41 mmol) in MeOH (5 mL) was added Et$_3$N (0.6 ml). The reaction mixture was stirred at room temperature for 15 minutes. The MeOH was removed by rotary evaporation and the residue was put in high vacuum line for 30 minutes. The residue was dissolved in anhydrous AcCN (1 ml) and denoted as solution A for the next reaction.

To a solution of DSC (250 mg, 0.976 mmol) and Boc-AA-14 (250 mg, 0.718 mmol) in anhydrous AcCN (2 mL) was added Et$_3$N (0.28 ml). The reaction mixture was stirred at room temperature for 2.5 hours and then Et$_3$N (0.2 ml) and solution A were added to the reaction. The reaction was stirred at room temperature for 16 hours. Most of the solvent was removed by rotary evaporation. The residue was purified by flash column chromatography using CH$_2$Cl$_2$/MeOH (9/1) as an eluent to give the desired product (53) (41 mg, 19% yield). $^1$H-NMR (CDCl$_3$, 400 MHz) δ: 6.73–6.60 (m, 3H), 6.55 (b, NH, 1H), 5.93–5.90 (bs, 2H), 5.25 (b, NH, 1H), 4.40, 4.15 (m, 1H), 3.66–3.29 (m, 12H), 2.67–2.33 (m, 6H), 1.42 (s, 9H), 1.23–1.12(m, 6H).

Preparation of MDEA-AA-14-NH$_2$ (54)

To a solution of 53 (41 mg, 0.07625 mmol) in CH$_2$Cl$_2$ (1 ml) was added TFA (0.2 ml). The reaction mixture was stirred at room temperature for 1.5 hours. TLC analysis of the reaction showed that the starting material (53) disappeared and a new more polar spot displayed (silica gel, MeOH/CH$_2$Cl$_2$=1/9). Most of the CH$_2$Cl$_2$ and TFA were removed by rotary evaporation under reduced pressure. The residue was further dried under high vacuum for 18 hours to remove trace of TFA. This gave the desired product (54) (40 mg, 95% yield). $^1$H-NMR (CDCl$_3$, 400 MHz) δ: 6.74–6.70 (m, 1H), 6.60–6.55 (m, 2H), 5.93–5.90 (bs, 2H), 4.30, 4.06 (m, 1H), 3.76–3.21 (m, 12H), 2.81–2.51 (m, 6H), 1.23–1.12 (m, 6H).

Preparation of MDA, MDMA and MDEA Particle Reagents

Direct Coupling of MDA MDMA and MDEA to PRM a) MDA Latex Particle (44)

MDA particle reagents of various levels of immobilization are prepared by dropwise and sequential addition of GAFAC (0.507–0.529 mL, 14.7% stock solution, 0.7% in reaction),MDA (0.139–0.580 mL, 77.27 mM stock solution; 1, 2, 3, and 4 mM in reaction), and DA-10 (0.099–0.104 mL, 324.4 mM stock solution, 3 mM in reaction) into diafiltered particle raw material (PRM) (10 ml, 10.3% stock solution, 9.62–9.24% solids in reaction). The pH is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication. This supernatant exchange process is repeated 3 more times. The final pellets are resuspended into wash buffer (20 ml) resulting in particle concentrate solutions (20 ml, 50 mg/ml).

b) MDMA Latex Particle (45)

MDMA particle reagents of various level of immobilization are prepared by dropwise and sequential addition of GAFAC (0.48–0.502 mL, 14.7% stock solution, 0.7% in reaction), MDMA (0.148–0.620 ml, 72.56 mM stock solution; 1, 2, 3, and 4 mM in reaction), and DA-10 (0.122–0.128 ml, 324.4 mM stock solution, 3 mM in reaction) into diafiltered particle raw material (10 ml, 10.3% stock solution, 9.62–9.24% solids in reaction). The pH is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication. This supernatant exchange process is repeated 3 more times. The final pellets are resuspended into wash buffer (20 ml) resulting in particle concentrate solutions (20 ml, 50 mg/mL).

c) MDEA Latex Particle (46)

MDEA particle reagents of various level of immobilization are prepared by dropwise and sequential addition of GAFAC (0.508–0.533 ml, 14.7% stock solution, 0.7% in reaction), MDEA (0.157–0.661 ml, 68.4 mM stock solution; 1, 2, 3, and 4 mM in reaction), and DA-10 (0.100–0.104 ml, 324.4 mM stock solution, 3 mM in reaction) into diafiltered particle raw material (10 ml, 10.3% stock solution, 9.62–9.24% solids in reaction). The pH is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication: This supernatant exchange process is repeated 3 more times. The final pellets are resuspended into wash buffer (20 ml) resulting in particle concentrate solutions (20 ml, 50 mg/mL).

Coupling of MDA, MDMA and MDEA with a Linker to PRM a) MDA-AA-14-NH$_2$ Latex Particle (49)

MDA-AA-14-NH$_2$ particle reagents of various level of immobilization are prepared by dropwise and sequential addition of GAFAC (0.507–0.527 ml, 14.7% stock solution, 0.7% in reaction), MDA-AA-14-NH$_2$ (0.132–0.549 ml, 81.4 mM stock solution; 1, 2, 3, and 4 mM in reaction), and DA-10 (0.099–0.103 ml, 324.4 mM stock solution, 3 mM in reaction) into diafiltered particle raw material (10 ml, 10.3% stock solution, 9.62–9.24% solids in reaction). The pH value is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication. This supernatant exchange process is repeated 3 more times. The final pellets are resuspended into wash buffer (20 ml) resulting in particle concentrate solutions (20 ml, 50 mg/mL).

b) MDMA-AA-14-NH$_2$ Latex Particle (52)

MDMA-AA-14-NH$_2$ particle reagents of various level of immobilization are prepared by dropwise and sequential addition of GAFAC (0.505–0.520 ml, 14.7% stock solution, 0.7% in reaction), MDA-AA-14-NH$_2$ (0.096–0.396 ml, 111.6 mM stock solution; 1, 2, 3, and 4 mM in reaction), and DA-10 (0.122–0.125 ml, 264.0 mM stock solution, 3 mM in reaction) into diafiltered particle raw material (10 ml, 10.3% stock solution, 9.62–9.24% solids in reaction). The pH is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication. This supernatant exchange process is repeated 3 more times. The final pellets are resuspended into wash buffer (20 ml) resulting in particle concentrate solutions (20 ml, 50 mg/mL).

c) MDEA-AA-14-NH$_2$ Latex Particle (55)

MDEA-AA-14-NH$_2$ particle reagents of two levels of immobilization are prepared by dropwise and sequential addition of GAFAC (0.515 and 0.531 ml, 14.7% stock solution, 0.7% in reaction), MDEA-AA-14-NH$_2$ (0.301 and 0.621 ml, 72.53 mM stock solution; 2 and 4 mM in reaction), and DA-10 (0.101 and 0.104 ml, 324.4 mM stock solution, 3 mM in reaction) into diafiltered particle raw material (10 ml, 10.3% stock solution, 9.62–9.24% solids in reaction). The pH is measured and adjusted to 9.2. The reactions are carried out at 70° C. for 18 hours. Each supernatant (10 ml) is separated by centrifugation (28,000 rpm) and decanting. Fresh wash buffer (20 ml, 1.0% GAFAC, 15 mM phosphate buffer, 0.2% Proclin, 0.006% neomycin sulfate) is added to each reaction tube and the particle reagents resuspended by sonication. This supernatant exchange process is repeated 3 more times. The final pellets are resuspended into wash buffer (20 ml) resulting in particle concentrate solutions (20 ml, 50 mg/mL).

The antibodies and particle conjugates may be employed in assays for the detection of the respective analytes.

Preparation of Bromoacetyl G6PDH

Figure 9:
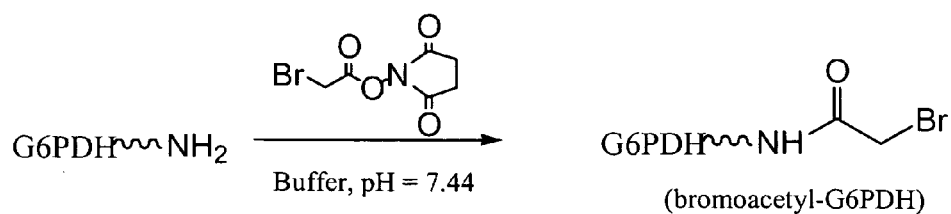
FIG. 9 is a reaction scheme depicting an example of a preparation of bromoacetyl-G6PDH.

Referring to FIG. 9, a mixture of 2.1 ml of G6PDH, (11.8 mg/ml) containing 24.78 mg protein, in 100 mM phosphate-1.0 mM EDTA, pH 7.44 and 0.32 ml of bromoacetic acid N-hydroxy succinimide (5 mg/ml) in DMF was incubated at room temperature for 3 hours. The protein mixture was buffer exchanged with 100 mM phosphate-5.0 mM EDTA, pH 6.0 in an Amicon ultrafiltration system fitted with a YM10 membrane. Buffer exchange was continued to concentrate to 3 ml. This yielded bromoacetyl-G6PDH (21.6 mg, 7.2 mg/ml).

3) Preparation of G6PDH Conjugate from Compounds (9) and (40)

Figure 10:
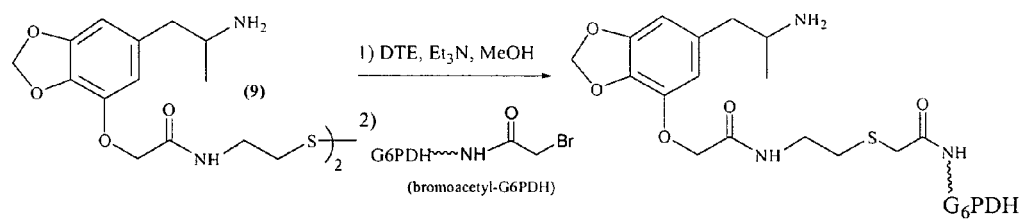
FIG. 10 is a reaction scheme depicting an example of a preparation of a G6PDH conjugate of compound (9).
Figure 11:
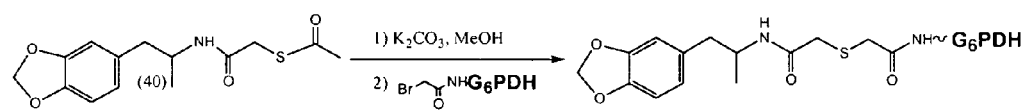
FIG. 11 is a reaction scheme depicting an example of a preparation of a G6PDH conjugate of Compound (40).

Referring to FIG. 10, a mixture of dimer (9) (29.5 mg, 0.0474 mmol) was dissolved in methanol (6 ml). To this stirring solution was added a solution of 7.7 mg of DTE in methanol (1 ml) and triethyl amine (10 µL) under nitrogen. This mixture was stirred at room temperature for 2 hours. The methanol was evaporated and put in vacuum for 1 hour. To this compound was added bromoacetyl G6PDH (prepared as described above) (1.4 ml, 7.2 mg/ml, 10.08 mg protein) and 0.6 ml of 100 mM phosphate-5.0 mM EDTA, pH 7.60). The pH was adjusted from 7.32 to 7.72. The mixture was stirred at 4° C. for 18 hours. The mixture was diluted with 50 mM-phosphate and 100 mM NaCl, pH=7.0. The protein mixture was buffer exchanged with 50 mM phosphate-100 mM NaCl, pH 7.0 in an Amicon ultrafiltration system fitted with a YM10 membrane until negative reaction of DTDP was observed. This gave 3 ml of G6PDH conjugate (1.68 mg/ml, protein 5.04 mg) Referring to FIG. 11, to a solution of 40 (16.7 mg, 0.0565 mmol) in methanol (1 ml) was added $K_2CO_3$ (20 mg) and water (50 μL) under nitrogen. The reaction mixture was stirred at room temperature for 1.5 hour. The methanol was evaporated to dryness and the compound was dissolved in DMF (0.2 ml). To this solution was added bromoacetyl G6PDH (prepared as described above) (1.5 ml, 7.2 mg/ml, 10.8 mg protein) and 0.62 ml of 100 mM phosphate-5.0 mM EDTA, pH 7.60). The pH was adjusted from 7.41 to 7.70. The mixture was stirred at 4° C. for 16 hours. The mixture was centrifuged and filtered. The solution was diluted with 50 mM-phosphate and 100 mM NaCl, pH=7.0. The protein mixture was buffer exchanged with 50 mM phosphate-100 mM NaCl, pH 7.0 in an Amicon ultrafiltration system fitted with a YM10 membrane until negative reaction of DTDP was observed. This gave 3 ml of G6PDH conjugate (3.34 mg/ml, protein 10 mg).

A conjugate of compound (22) and G6PDH was also prepared by a procedure similar to that described above.

Assay Using Reagents in Accordance with Embodiments of the Present Invention

The antibodies and enzyme conjugates in accordance with the invention may be employed in assays for the detection of the respective analytes. The immunogen is injected into sheep to raise antibody. The antibody obtained from the sheep bleed is spiked into the antibody diluent to prepare the antibody reagent. The antibody reagent consists of antibody as prepared above, buffer, stabilizers, preservatives, and the substrates for the enzyme conjugate NAD and glucose 6 phosphate.

Enzyme conjugate from a compound of the invention is spiked into the conjugate reagent to prepare the enzyme conjugate reagent. The enzyme conjugate reagent consists of the conjugate, buffer, stabilizers and preservatives.

The antibody reagent and enzyme conjugate reagent are used in a homogeneous assay format to detect Ecstasy in urine samples. The analyzer (instrument) used to set up the assay is Syva 30-R Biochemical Analyzer (Syva Company, Cupertino Calif.). Ecstasy containing urine sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of $NAD^+$ to NADH, which can be measured at 340 nm. The change in the absorbance at 340 nm can be measured spectrophotometrically. The Ecstasy concentration in a urine specimen can be measured in terms of G6PDH activity. The increase in the rate at 340 nm is due to the formation of NADH and is proportional to the enzyme conjugate activity. An assay curve is generated using MDMA spiked into negative urine. The assay rate increases with increasing the concentration of free drug in the sample.

The above discussion includes certain theories as to mechanisms involved in the present invention. These theories should not be construed to limit the present invention in any way, since it has been demonstrated that the present invention achieves the results described.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A compound of the formula:

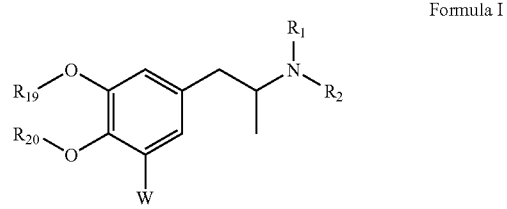

Formula I wherein:

$R^{19}$ is lower alkyl or is taken together with $R^{20}$ to form a ring, which may be a five- or six-member ring, usually a five-member ring;

$R^{20}$ is lower alkyl, or is taken together with $R^{19}$ to form a ring as discussed above, $R^1$ is H or lower alkyl, $R^2$ is (a) $-(CH_2)_aC(O)(CH_2)_bSR^3$, wherein a is 0 to 5, b is 1 to 5 and $R^3$ is lower alkyl or $(CH_2)_cC(O)NR^4R^5$ wherein c is 1 to 5, $R^4$ is H or lower alkyl and $R^5$ is H, an immunogenic carrier or a label, or (b) $(A)_d(Q)_n$, wherein Q is H or $-(CH_2)_eCH(R^8)(CH_2)_f OC(O)(CH_2)_gR^9$ being H only when d is 1 wherein A is $-C(O)(CH_2)_hC(O)NR^{10}((CH_2)_jO(CH_2)_kO)_m (CH)_2NR^{11}-$, d is 0 or 1, n is 0 or 1 wherein one of d or n is 1, h is 1 to 5, $R^{10}$ is H or lower alkyl, j is 1 to 5, k is 1 to 5, m is 1 to 3, $R^{11}$ is H or lower alkyl, e is 1 to 5, $R^8$ is OH or H, f is 1 to 5, g is 0 to 5, and $R^9$ is H, an immunogenic carrier or a label;

W is H or $JR^{14}$ being H when $R^2$ is other than H or lower alkyl, wherein

J is O or S, $R^{14}$ is H, lower alkyl, a protecting group, or $-(CH_2)_r C(O)NR^{15}(CH_2)_s(D)_tR^{16}$, wherein r is 1 to 5, $R^{15}$ is H or lower alkyl, s is 1 to 5, D is S, O, or NH, t is 0 or 1 being 0 when $R^{16}$ is maleimidyl or succinimidyl, $R^{16}$ is H, maleimidyl, succinimidyl, or $-(CH_2)_q C(O)NR^{17}R^{18}$, q is 1 to 5, $R^{17}$ is H or lower alkyl, $R^{18}$ is H, lower alkyl, an immunogenic carrier or label, and including the acid salts thereof.

2. A compound according to claim 1 wherein $R^1$ is H.

3. A compound according to claim 1 wherein $R^{16}$ is $-(CH^2)_qC(O)NR^{17}R^{18}$ and $R^{18}$ is a poly(amino acid).

4. A compound according to claim 1 wherein $R^1$ is H or lower alkyl, W is H and $R^2$ is $-(CH_2)_aC(O)(CH_2)_bSR^3$, wherein $R^3$ is $-(CH_2)_cC(O)NR^4R^5$ wherein $R^4$ is H or lower alkyl and $R^5$ is a poly(amino acid).

5. A compound according to claim 1 wherein $R^1$ is H or lower alkyl, W is H and $R^2$ is $-(CH_2)_aC(O)(CH_2)_bSR^3$, wherein $R^3$ is $-(CH_2)_cC(O)NR^4R^5$ wherein $R^4$ is H or lower alkyl and $R^5$ is an immunogenic carrier.

6. A compound according to claim 1 wherein $R^1$ is H or lower alkyl, W is H and $R^2$ is $(A)_d(Q)_n$ wherein d is 0, n is 1, Q is $-(CH_2)_eCH(R^8)(CH_2)_fOC(O)(CH_2)_gR^9$ and $R^9$ is a poly(amino acid).

7. A compound according to claim 1 wherein $R^1$ is H or lower alkyl, W is H and $R^2$ is $(A)_d(Q)_n$ wherein d is 1, n is 1, Q is $-(CH_2)_eCH(R^8)(CH_2)_fOC(O)(CH_2)_gR^9$ and A is $-C(O)(CH_2)_hC(O)NR^{10}((CH_2)_jO(CH_2)_kO)_m(CH)_2NR^{11}-$, and $R^9$ is a poly(amino acid).

8. A compound of the formula:

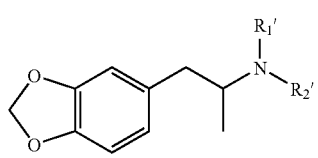

Formula II wherein:
$R^{1'}$ is H, lower alkyl or a protecting group,
$R^{2'}$ is
(a) $-(CH_2)_aC(O)(CH_2)_bSR^{3'}$, wherein a is 0 to 5, b is 1 to 5 and $R^{3'}$ is lower alkyl or $(CH_2)_cC(O)NR^{4'}R^{5'}$ wherein c is 1 to 5, $R^{4'}$ is H or lower alkyl and $R^{5'}$ is H, an immunogenic carrier or a label, or
(b) $(A)_d(Q)_n$ wherein Q is H or $-(CH_2)_eCH(R^{8'})(CH_2)_fOC(O)(CH_2)_gR^{9'}$ being H only when d is 1 wherein A is $-C(O)(CH_2)_hC(O)N(R^{10})((CH_2)_jO(CH_2)_kO)_m(CH_2)_2NR^{11}-$, d is 0 or 1, n is 0 or 1 wherein one of d or n is 1, h is 1 to 5, $R^{10}$ is H or lower alkyl, j is 1 to 5, k is 1 to 5, m is 1 to 3, $R^{11}$ is H or lower alkyl, e is 1 to 5, $R^{8'}$ is OH or H, f is 1 to 5, g is 0 to 5, and $R^{9'}$ is H, an immunogenic carrier or a label,
and including the acid salts thereof.

9. A compound according to claim 8 wherein $R^{1'}$ is H or lower alkyl and $R^{2'}$ is $(-CH_2)_aC(O)(CH_2)_bSR^{3'}$ wherein a is 0, b is 1.

10. A compound according to claim 8 wherein $R^{1'}$ is H or lower alkyl and $R^{2'}$ is $-(CH_2)_aC(O)(CH_2)_bSR^{3'}$ wherein a is 0, b is 1, $R^{3'}$ is $(CH_2)_cC(O)NR_4'R^{5'}$ wherein c is 1, $R^{4'}$ is H and $R^{5'}$ is a poly(amino acid).

11. A compound according to claim 10 wherein said poly(amino) acid is an enzyme or an immunogenic carrier.

12. A compound according to claim 8 wherein $R^{1'}$ is H or lower alkyl and $R^{2'}$ is $-(CH_2)_aC(O)(CH_2)_bSR^{3'}$ wherein a is 0, b is 1, $R^{3'}$ is $(CH_2)_cC(O)NR^{4'}R^{5'}$ wherein c is 1, $R^{4'}$ is H and $R^{5'}$ is an immunogenic carrier.

13. A compound according to claim 8 wherein $R^{1'}$ is H or lower alkyl and $R^{2'}$ is $-(CH_2)_aC(O)(CH_2)_bSR^{3'}$ wherein a is 0, b is 1, $R^{3'}$ is $(CH_2)_cC(O)NR^{4'}R^{5'}$ wherein c is 1, $R^{4'}$ is H and $R^{5'}$ is a particle label or a particle immunogenic carrier.

14. A compound according to claim 8 wherein $R^{1'}$ is H or lower alkyl and $R^{2'}$ is $(A)_d(Q)_n$ wherein d is 0, n is 1, Q is $-(CH_2)_eCH(R^{8'})(CH_2)_fOC(O)(CH_2)_gR^{9'}$, e is 1, $R^{8'}$ is OH, f is 1, g is 0 and $R^{9'}$ is a poly(amino) acid.

15. A compound according to claim 14 wherein said poly(amino) acid is an enzyme or an immunogenic carrier.

16. A compound according to claim 8 wherein $R^{1'}$ is H or lower alkyl and $R^{2'}$ is $(A)_d(Q)_n$ wherein d is 0, n is 1, Q is H, A is $-C(O)(CH_2)_hC(O)NR^{10}((CH_2)_jO(CH_2)_kO)_m(CH)_2NR^{11}-$, $R^{10'}$ is H, h is 2, m is 1, j is 2, k is 2, $R^{10''}$ is H.

17. A compound according to claim 8 wherein $R^{1'}$ is H or lower alkyl and $R^{2'}$ is $(A)_d(Q)_n$ wherein d is 1, n is 1, Q is $-(CH_2)_eCH(R^{8'})(CH_2)_fOC(O)(CH_2)_gR^{9'}$, e is 1, $R^{8'}$ is OH, f is 1, g is 0, A is $-C(O)(CH_2)_hC(O)NR^{10}((CH_2)_jO(CH_2)_kO)_m(CH)_2NR^{11}-$, $R^{10'}$ is H, h is 2, m is 1, j is 2, $R^{10''}$ H and $R^{9'}$ is a poly(amino) acid or a particle label or a particle immunogenic carrier.

18. A compound according to claim 17 wherein $R^{9'}$ is a poly(amino) acid, which is an enzyme or an immunogenic carrier.

19. A compound according to claim 17 wherein $R^{9'}$ is a particle label or a particle immunogenic carrier.

20. A compound of the formula:

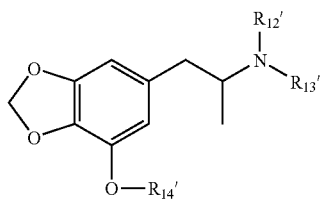

Formula III wherein:
$R^{12'}$ is H or lower alkyl,
$R^{13'}$ is H or lower alkyl,
$R^{14'}$ is a protecting group, or $-(CH_2)_rC(O)NR^{15'}(CH_2)_s(D)_tR^{16'}$, wherein r is 1 to 5, $R^{15'}$ is H or lower alkyl, s is 1 to 5, D is S, O, or NH, t is 0 or 1 being 0 when $R^{16'}$ is maleimidyl or succinimidyl, $R^{16'}$ is H, a protecting group, maleimidyl or succinimidyl, or $-(CH_2)_qC(O)NR^{17'}R^{18'}$ wherein q is 1 to 5,
$R^{17'}$ is H, lower alkyl or a protecting group,
$R^{18'}$ is H, lower alkyl, a protecting group, an immunogenic carrier or a label,
and including the acid salts thereof.

21. A compound according to claim 20 wherein $R^{12'}$ is H and $R^{13'}$ is H or lower alkyl, $R^{14'}$ is $-(CH_2)_rC(O)NR^{15'}(CH_2)_s(D)_tR^{16'}$, wherein r is 1, $R^{15'}$ is H, s is 2, D is S, t is 1 and $R^{16'}$ is H.

22. A compound according to claim 20 wherein $R^{12'}$ is H and $R^{13'}$ is H or lower alkyl, $R^{14'}$ is $-(CH_2)_rC(O)NR^{15'}(CH_2)_s(D)_tR^{16'}$, wherein r is 1, $R^{15'}$ is H, s is 2, t is 0 and $R^{16'}$ is succinimidyl or maleimidyl.

23. A compound according to claim 20 wherein $R^{12'}$ is H and $R^{13'}$ is H or lower alkyl, $R^{14'}$ is $-(CH_2)_rC(O)NR^{15'}(CH_2)_s(D)_tR^{16'}$, wherein r is 1, $R^{15'}$ is H, s is 2, D is S, t is 1 and $R^{16'}$ is $-(CH_2)_qC(O)NR^{17'}R^{18'}$, q is 1, $R^{17'}$ is H and $R^{18'}$ is a poly(amino) acid or a particle label or a particle immunogenic carrier.

24. A compound according to claim 23 wherein $R^{18'}$ is a particle label or a particle immunogenic carrier.

25. An antibody raised against a compound according to claim 15 wherein said poly(amino) acid is an immunogenic carrier.

26. An antibody raised against a compound according to claim 18 wherein said poly(amino) acid is an immunogenic carrier.

27. An antibody raised against a compound according to claim 23 wherein $R^{17'}$ is a poly(amino) acid, which is an immunogenic carrier.

28. A reagent system comprising a compound according to claim 15 wherein said poly(amino) acid is an enzyme, an antibody for methylenedioxyamphetamine and/or an antibody for methylenedioxymethamphetamine and/or an antibody for methylenedioxyethamphetamine.

29. A reagent system comprising a compound according to claim 18 wherein said poly(amino) acid is an enzyme, an antibody for methylenedioxyamphetamine and/or an antibody for methylenedioxymethamphetamine and/or an antibody for methylenedioxyethamphetamine.

30. A reagent system comprising a compound according to claim 23 wherein $R^{17'}$ is a poly(amino) acid, which is an enzyme, an antibody for methylenedioxyamphetamine and/or an antibody for methylenedioxymethamphetamine and/or an antibody for methylenedioxyethamphetamine.

31. A method for determining methylenedioxyamphetamine and/or methylenedioxymethamphetamine and/or methylenedioxyethamphetamine in a sample suspected of containing methylenedioxyamphetamine and/or methylenedioxymethamphetamine and/or methylenedioxyethamphetamine, said method comprising:
 (a) providing in combination in a medium:
  (i) said sample and
  (ii) a reagent system according to claim 28; and
 (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine, the presence thereof indicating the presence of said methylenedioxyamphetamine and/or methylenedioxymethamphetamine and/or methylenedioxyethamphetamine in said sample.

32. A method according to claim 31 wherein said examining comprises measuring signal from said enzyme, the amount thereof being related to the presence of said methylenedioxyamphetamine and/or methylenedioxymethamphetamine and/or methylenedioxyethamphetamine in said sample.

33. A method according to claim 32 wherein said method is a homogeneous method and said medium is examined for the amount of said signal.

34. A method according to claim 32 wherein said method is a heterogeneous method and said complex, if present, is separated from said medium and said medium or said complex is examined for the amount of said signal.

35. A method for determining methylenedioxyamphetamine and/or methylenedioxymethamphetamine and/or methylenedioxyethamphetamine in a sample suspected of containing methylenedioxyamphetamine and/or methylenedioxy-methamphetamine and/or methylenedioxyethamphetamine, said method comprising:
 (a) providing in combination in a medium:
  (i) said sample and
  (ii) a reagent system according to claim 29; and
 (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

36. A method according to claim 35 wherein said examining comprises measuring signal from said enzyme, the amount thereof being related to the presence of said methylenedioxyamphetamine and/or methylenedioxymethamphetamine and/or methylene dioxyethamphetamine in said sample.

37. A method according to claim 36 wherein said method is a homogeneous method and said medium is examined for the amount of said signal.

38. A method according to claim 36 wherein said method is a heterogeneous method and said complex, if present, is separated from said medium and said medium or said complex is examined for the amount of said signal.

39. A method for determining methylenedioxyamphetamine and/or methylenedioxymethamphetamine in a sample suspected of containing methylenedioxyamphetamine and/or methylenedioxymethamphetamine and/or methylene dioxyethamphetamine, said method comprising:
 (a) providing in combination in a medium:
  (i) said sample and
  (ii) a reagent system according to claim 30; and
 (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxymethamphetamine and said antibody for methylenedioxymethamphetamine, the presence thereof indicating the presence of said methylenedioxyamphetamine and/or methylenedioxymethamphetamine in said sample.

40. A method according to claim 39 wherein said examining comprises measuring signal from said enzyme, the amount thereof being related to the presence of said methylenedioxyamphetamine and/or methylenedioxymethamphetamine and/or methylene dioxyethamphetamine in said sample.

41. A method according to claim 40 wherein said method is a homogeneous method and said medium is examined for the amount of said signal.

42. A method according to claim 40 wherein said method is a heterogeneous method and said complex, if present, is separated from said medium and said medium or said complex is examined for the amount of said signal.

43. A method for determining amphetamine and/or methamphetamine and/or methylenedioxyethamphetamine in a sample suspected of containing methylenedioxyamphetamine and/or methylenedioxymethamphetamine and/or methylene dioxyethamphetamine, said method comprising:
 (a) providing in combination in a medium:
  (i) said sample,
  (ii) an antibody for methylenedioxyamphetamine, and/or
  (iii) an antibody for methylenedioxymethamphetamine, and/or
  (iv) an antibody for methylenedioxyethamphetamine, and
  (v) a compound of the formula:

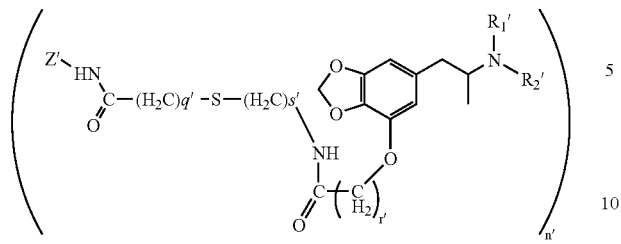

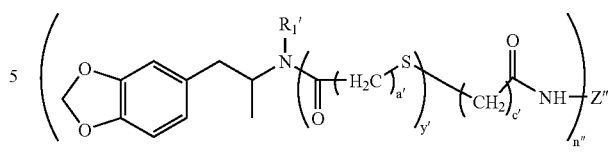

wherein:
$R^{1\prime}$ is H,
$R^{2\prime}$ is H, methyl or ethyl,
r' is 1 to 5,
s' is 1 to 5,
q' is 1 to 5,
Z' is an enzyme,
n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

44. A method according to claim 43 wherein said examining comprises measuring signal from said enzyme, the amount thereof being related to the presence of said methylenedioxyamphetamine and/or methylenedioxymethamphetamine and/or methylene-dioxyethamphetamine in said sample.

45. A method according to claim 44 wherein said method is a homogeneous method and said medium is examined for the amount of said signal.

46. A method according to claim 44 wherein said method is a heterogeneous method and said complex, if present, is separated from said medium and said medium or said complex is examined for the amount of said signal.

47. A method according to claim 43 wherein said enzyme is glucose-6-phosphate dehydrogenase.

48. A method for determining methylenedioxyamphetamine and/or methylenedioxymethamphetamine and/or methylenedioxyethamphetamine in a sample suspected of containing methylenedioxyamphetamine and/or methylene-dioxy-methamphetamine and/or methylenedioxyethamphetamine, said method comprising:

(a) providing in combination in a medium:
  (i) said sample,
  (ii) an antibody for methylenedioxyamphetamine, and/or
  (iii) an antibody for methylenedioxymethamphetamine, and/or
  (iv) an antibody for methylenedioxyethamphetamine, and
  (v) a compound of the formula:

wherein:
$R^{1\prime}$ is H, or methyl, or ethyl,
a' is 1 to 5,
y' is 1,
Z' is an enzyme,
c' is 1 to 5,
n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxymethamphetamine in said sample.

49. A method according to claim 48 wherein said examining comprises measuring signal from said enzyme, the amount thereof being related to the presence of said methylenedioxyamphetamine and/or methylenedioxymethamphetamine and/or methylenedioxyethamphetamine in said sample.

50. A method according to claim 49 wherein said method is a homogeneous method and said medium is examined for the amount of said signal.

51. A method according to claim 49 wherein said method is a heterogeneous method and said complex, if present, is separated from said medium and said medium or said complex is examined for the amount of said signal.

52. A method according to claim 48 wherein said enzyme is glucose-6-phosphate dehydrogenase.

53. A method for determining methylenedioxyamphetamine and/or methylenedioxymethamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:
  (i) said sample,
  (ii) conjugate of an enzyme and a methylenedioxyamphetamine analog and/or a conjugate of an enzyme and a methylenedioxymethamphetamine analog and/or a conjugate of an enzyme and a methylenedioxyethamphetamine analog,
  (i) an antibody for methylenedioxyamphetamine, said antibody being raised against a compound of the formula:

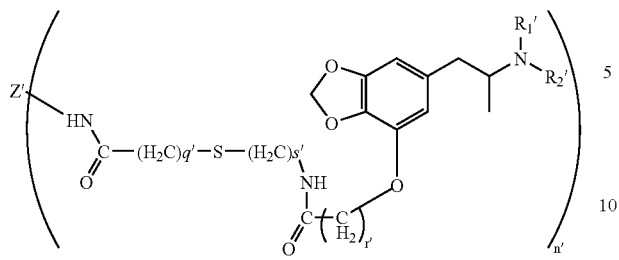

wherein:
R$_{1'}$ is H,
R$_{2'}$ is H,
r' is 1 to 5,
s' is 1 to 5,
q' is 1 to 5,
Z' is an immunogenic protein or a non-poly(amino acid) immunogenic carrier,
n'' is an integer between 1 and the molecular weight of said immunogenic protein or said immunogenic carrier divided by about 500; and/or (iv) an antibody for methylenedioxymethamphetamine, said antibody being raised against a compound of the formula:

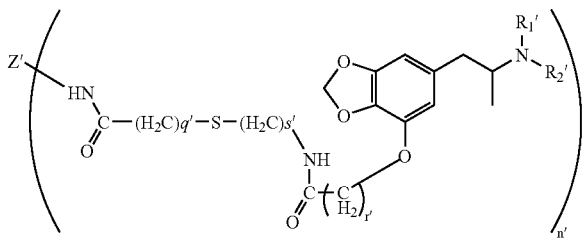

wherein:
R$_{1'}$ is H,
R$_{2'}$ is methyl,
r' is 1 to 5,
s' is 1 to 5,
q' is 1 to 5,
Z' is an immunogenic protein or a non-poly(amino acid) immunogenic carrier,
n'' is an integer between 1 and the molecular weight of said immunogenic protein or said immunogenic carrier divided by about 500; and/or (v) an antibody for methylenedioxyethamphetamine, said antibody being raised against a compound of the formula:

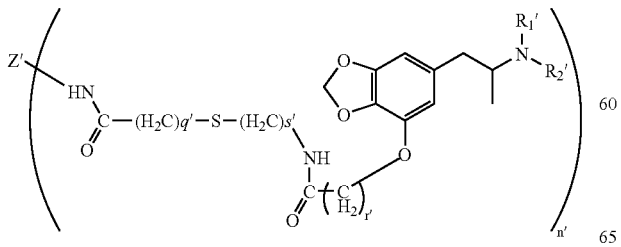

wherein:
R$_{1'}$ is H,
R$_{2'}$ is ethyl,
r' is 1 to 5,
s' is 1 to 5,
q' is 1 to 5,
Z' is an immunogenic protein or a non-poly(amino acid) immunogenic carrier,
n'' is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

54. A method according to claim 53 wherein said examining comprises measuring signal from said enzyme, the amount thereof being related to the presence of said methylenedioxyamphetamine and/or methylenedioxymethamphetamine and/or methylenedioxyethamphetamine in said sample.

55. A method according to claim 54 wherein said method is a homogeneous method and said medium is examined for the amount of said signal.

56. A method according to claim 54 wherein said method is a heterogeneous method and said complex, if present, is separated from said medium and said medium or said complex is examined for the amount of said signal.

57. A method according to claim 54 wherein said enzyme is glucose-6-phosphate dehydrogenase.

58. A method for determining methylenedioxyamphetamine and/or methylenedioxymethamphetamine in a sample suspected of containing methylenedioxyamphetamine and/or methylenedioxymethamphetamine, said method comprising:

(a) providing in combination in a medium:
  (i) said sample,
  (ii) a conjugate of an enzyme and an methylenedioxyamphetamine analog and/or a conjugate of an enzyme and a methylenedioxymethamphetamine analog and/or a conjugate of an enzyme and a methylenedioxyethamphetamine analog,
  (i) an antibody for methylenedioxyamphetamine, said antibody being raised against a compound of the formula:

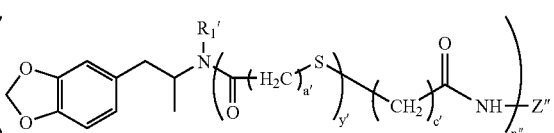

wherein:
R$_{1'}$ is H,
a' is 1 to 5,
y' is 1,

Z" is an immunogenic protein or a non-poly(amino acid) immunogenic carrier, c' is 1 to 5, n" is an integer between 1 and the molecular weight of said immunogenic protein or said immunogenic carrier divided by about 500; and/or (iv) an antibody for methylenedioxymethamphetamine, said antibody being raised against a compound of the formula:

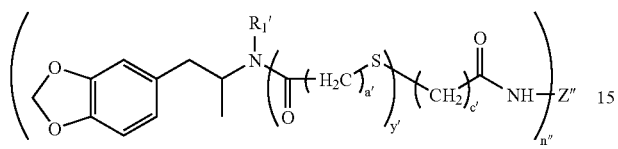

wherein:

R¹' is methyl, a' is 1 to 5, y' is 1,

Z" is an immunogenic protein or a non-poly(amino acid) immunogenic carrier, c' is 1 to 5, n" is an integer between 1 and the molecular weight of said immunogenic protein or said immunogenic carrier divided by about 500; and/or (v) an antibody for methylenedioxyethamphetamine, said antibody being raised against a compound of the formula:

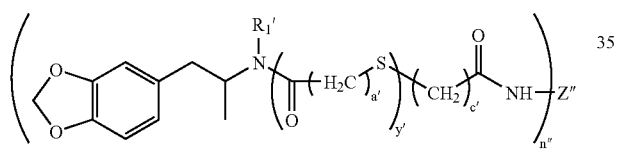

wherein:

R¹' is ethyl, a' is 1 to 5, y' is 1,

Z" is an immunogenic protein or a non-poly(amino acid) immunogenic carrier, c' is 1 to 5, n" is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said amphetamine and/or methamphetamine and/or methylenedioxyethamphetamine in said sample.

59. A method according to claim 58 wherein said examining comprises measuring signal from said enzyme, the amount thereof being related to the presence of said methylenedioxyamphetamine and/or methylenedioxymethamphetamine and/or methylenedioxyethamphetamine in said sample.

60. A method according to claim 59 wherein said method is a homogeneous method and said medium is examined for the amount of said signal.

61. A method according to claim 59 wherein said method is a heterogeneous method and said complex, if present, is separated from said medium and said medium or said complex is examined for the amount of said signal.

62. A method according to claim 58 wherein said enzyme is glucose-6-phosphate dehydrogenase.

63. A kit comprising in packaged combination:

(i) an antibody for methylenedioxyamphetamine, and/or (ii) an antibody for methylenedioxymethamphetamine, and/or (iii) an antibody for methylenedioxyethamphetamine, and (iv) a compound of the formula:

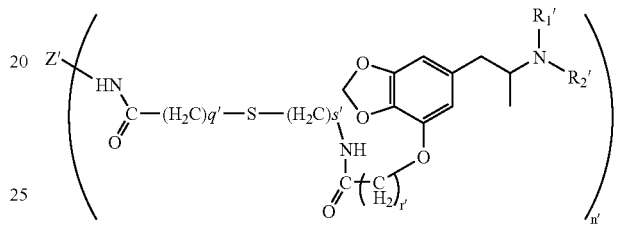

wherein:

R¹' is H,

R²' is H, methyl, or ethyl, r' is 1 to 5, s' is 1 to 5, q' is 1 to 5,

Z' is an enzyme such as, for example, glucose-6-phosphate dehydrogenase, n' is an integer between 1 and the molecular weight of said enzyme divided by about 500.

64. A kit according to claim 63 wherein said enzyme is glucose-6-phosphate dehydrogenase.

65. A kit comprising in packaged combination:

(i) an antibody for methylenedioxyamphetamine, (ii) an antibody for methylenedioxymethamphetamine, and/or (iii) an antibody for methylenedioxyethamphetamine, and (iv) a compound of the formula:

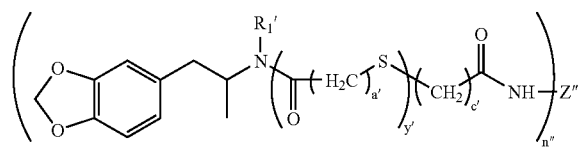

wherein:

R¹' is H, methyl or ethyl, a' is 1 to 5, usually 1, y' is 1,

Z' is an enzyme such as, for example, glucose-6-phosphate dehydrogenase, c' is 1 to 5, n' is an integer between 1 and the molecular weight of said enzyme divided by about 500.

66. A kit according to claim 65 wherein said enzyme is glucose-6-phosphate dehydrogenase.

67. A kit comprising in packaged combination:

(i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog; and (ii) an antibody for methylenedioxyamphetamine, said antibody being raised against a compound of the formula:

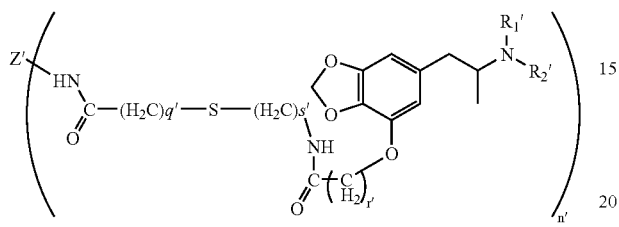

wherein:
$R^{1\prime}$ is H,
$R^{2\prime}$ is H,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500; and/or (iii) an antibody for methylenedioxymethamphetamine, said antibody being raised against a compound of the formula:

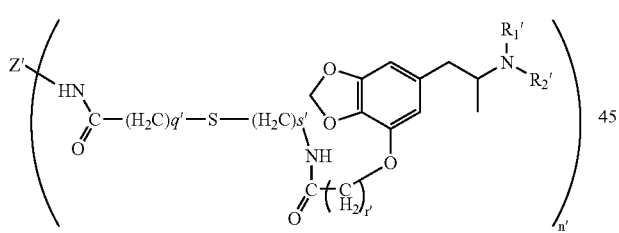

wherein:
$R^{1\prime}$ is H,
$R^{2\prime}$ is methyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500, and/or (iv) an antibody for methylenedioxyethamphetamine, said antibody being raised against a compound of the formula:

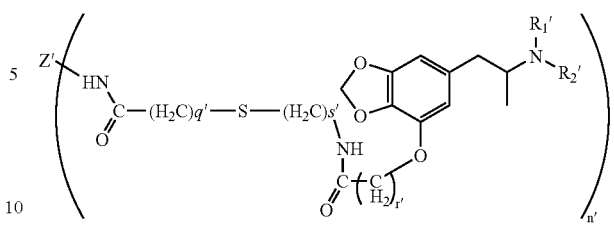

wherein:
$R^{1\prime}$ is H,
$R^{2\prime}$ is ethyl,
r' is 1 to 5,
s' is 1 to 5,
q' is 1 to 5,
Z' is an immunogenic protein or a non-poly(amino acid) immunogenic carrier,
n" is an integer between 1 and the molecular weight of said immunogenic protein or said immunogenic carrier divided by about 500.

68. A kit comprising in packaged combination:

(i) a conjugate of an enzyme and an methylenedioxyamphetamine analog and/or a conjugate of an enzyme and a methylenedioxymethamphetamine analog, and (ii) an antibody for methylenedioxyamphetamine, said antibody being raised against a compound of the formula:

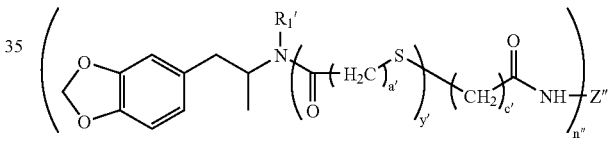

wherein:
$R^{1\prime}$ is H,
a' is 1 to 5,
y' is 1,
Z" is an immunogenic protein or a non-poly(amino acid) immunogenic carrier,
c' is 1 to 5,
n" is an integer between 1 and the molecular weight of said immunogenic protein or said immunogenic carrier divided by about 500; and/or (iii) an antibody for methylenedioxymethamphetamine, said antibody being raised against a compound of the formula:

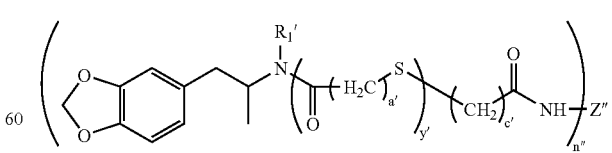

wherein:
$R^{1\prime}$ is methyl,
a' is 1 to 5,
y' is 1,

Z" is an immunogenic protein or a non-poly(amino acid) immunogenic carrier, c' is 1 to 5, n" is an integer between 1 and the molecular weight of said immunogenic protein or said immunogenic carrier divided by about 500, and/or (iv) an antibody for methylenedioxyethamphetamine, said antibody being raised against a compound of the formula:

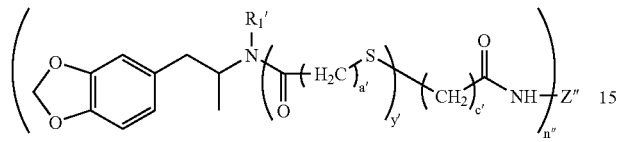

wherein:

R$^{1''}$ is ethyl, a' is 1 to 5, y' is 1,

Z" is an immunogenic protein or a non-poly(amino acid) immunogenic carrier, c' is 1 to 5, n" is an integer between 1 and the molecular weight of said immunogenic protein or said immunogenic carrier divided by about 500.

* * * * *